(12) United States Patent
Zaghouani et al.

(10) Patent No.: US 8,609,091 B2
(45) Date of Patent: *Dec. 17, 2013

(54) METHOD FOR ENDOCYTIC PRESENTATION OF AN IMMUNOSUPPRESSIVE FOR THE TREATMENT OF TYPE 1 DIABETES

(75) Inventors: Habib Zaghouani, Columbia, MO (US); Randal Keith Gregg, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 1367 days.

This patent is subject to a terminal disclaimer.

(21) Appl. No.: 10/681,788

(22) Filed: Oct. 8, 2003

(65) Prior Publication Data

US 2004/0126374 A1  Jul. 1, 2004

Related U.S. Application Data

(63) Continuation-in-part of application No. PCT/US03/10700, filed on Apr. 8, 2003.

(60) Provisional application No. 60/371,663, filed on Apr. 9, 2002.

(51) Int. Cl.
    *A61K 39/00* (2006.01)

(52) U.S. Cl.
    USPC ...................................... 424/133.1

(58) Field of Classification Search
    None
    See application file for complete search history.

(56) References Cited

U.S. PATENT DOCUMENTS

| 5,817,308 | A | 10/1998 | Scott et al. |
| 5,969,109 | A | 10/1999 | Bona et al. |
| 6,737,057 | B1 | 5/2004 | Zaghouani |
| 2002/0038002 | A1 | 3/2002 | Zaghouani |
| 2002/0081298 | A1 | 6/2002 | Zaghouani |
| 2003/0103967 | A1 | 6/2003 | Zaghouani |
| 2005/0031605 | A1 | 2/2005 | Bunn et al. |
| 2005/0037448 | A1 | 2/2005 | Bouanani et al. |
| 2006/0115478 | A1 | 6/2006 | Zaghouani |

FOREIGN PATENT DOCUMENTS

| EP | 0741788 B1 | 2/2005 |
| WO | 9009804 A1 | 9/1990 |
| WO | WO9009804 | 9/1990 |
| WO | 9521926 A1 | 8/1995 |
| WO | 9830706 A1 | 7/1998 |
| WO | WO 02/053092 | * 7/2002 |
| WO | 2004004642 A2 | 1/2004 |

OTHER PUBLICATIONS

Kaufman, D.L., et al. J. Clin. Invest. Jan. 1992;89:283-292.*
Marketletter, Marketletter Pubs (UK) Sep. 13, 1999.*
Dong, V.M., et al. Ped. Transplan. 1999;3:181-192.*
Legge, K.L., et al. J. Immunol. 1998;161:106-111. Anderton, S.M. Immunology. 2001;104:367-376.*
Couzin, J. Science. 2003; 300:1862-1865.*
Harrison, L.C. Immunol Cell. Biol. 2008; 86:139-145.*
Skylar, J.S., et al. Diabetes Care. 2005;28(5):1068-1076.*
Skyler, J.S., et al. Diabetes Care. 2005;28:1068-1076.*
Goodnow, C.C. Lancet. 2001;357:2115-2121.*
Pozzilli, P., et al. Diabetol. 2000;43:1000-1004.*
Kraus, T.A., and Mayer, L. Curr. Opin. Gastroenterol. 2005;21:692-696.*
Bell, J.J. et al. J. Immunol. 2008;180:1508-1516.*
von Herrath, M. and Nepom, G.T. Nature Immunol. 2009;10(2):129-132.*
Leslie, M. Science. 2009;327:1573.*
van der Worp, H.B., et al. PLoS Med. 2010;7(3):1-8.*
Chao, C.-C., et al. Proc. Nat'l. Acad. Sci. 1999;96:9299-9304.*
Balasa, B., et al., "A Mechanism for IL-10-Mediated Diabetes in the Nonobese Diabetic (NOD) Mouse: ICAM-1 Deficiency Blocks Accelerated Diabetes," The Journal of Immunology, vol. 165, pp. 7330-7337 (2000).
Bu, Ding-Fang, et al., "Two Human Glutamate Decarboxylases, 65-kDa GAD and 67-kDa GAD, Are Each Encoded by a Single Gene," Proc. Natl. Acad. Sci. USA, vol. 89, pp. 2115-2119 (1992).
Gregg, Randal, et al., "IL-10 Diminishes CTLA-4 Expression on Islet-Resident T Cells and Sustains Their Activation Rather Than Tolerance," The Journal of Immunology, vol. 174, pp. 662-670 (2005).
Gregg, Randal, et al., "A Sudden Decline in Active Membrane-Bound TGF-β Impairs Both T Regulatory Cell Function and Protection Against Autoimmune Diabetes," The Journal of Immunology, vol. 173, pp. 7308-7316 (2004).
Kaufman, D., et al., "AutoImmunity to Two Forms of Glutamate Decarboxylase in Insulin-Dependent Diabetes Mellitus," Journal of Clinical Investigation, vol. 89, pp. 283-292 (1992).
Legge, K., et al., "Coupling of Peripheral Tolerance to Endogenous Interleukin 10 Promotes Effective Modulation of Myelin-Activated T Cells and Ameliorates Experimental Allergic Encephalomyelitis," J. Exp. Med., vol. 191, No. 12, pp. 2039-2051 (2000).
Legge, K., et al., "Multi-Modal Antigen Specific Therapy for Autoimmunity," Intern. Rev. Immunol., vol. 20, pp. 593-611 (2001).
Zambidis, E., et al., "Epitope-Specific Tolerance Induction with an Engineered Immunoglobulin," Proc. Natl. Acad. Sci. USA, Immunology, vol. 93, pp. 5019-5024 (1996).
Alleva, D.G., A. Gaur, L. Jin, D. Wegmann, P.A. Gottlieb, A. Pahuja, E.B. Johnson, T. Motheral, A. Putnam, P.D. Crowe, N. Ling, S.A. Boehme, and P.J. Conlon. (2002). Immunological characterization and therapeutic activity of an altered-peptide ligand, NBI6024, based on the immunodominant type 1 diabetes autoantigen insulin 13-chain (9-23) peptide. *Diabetes.* 51: 2126-2134.

(Continued)

*Primary Examiner* — Daniel E Kolker
(74) *Attorney, Agent, or Firm* — Perkins Coie LLP

(57) ABSTRACT

The present invention relates generally to methods and compositions for treatment, prevention, suppression, and/or delaying the onset of type 1 diabetes. More specifically, the present invention relates to the administration of a fusion protein comprising at least one immunoglobulin having one or more diabetogenic epitopes inserted within the variable region, for suspending, preventing or delaying the onset of type 1 diabetes.

23 Claims, 12 Drawing Sheets

(56) References Cited

OTHER PUBLICATIONS

Andre, I., A. Gonzalez, B. Wang, J. Katz, C. Benoist, and D. Mathis. 1996. Checkpoints in the progression of autoimmune disease: lessons from diabetes models. *Proc. Natl. Acad. Sci. USA*. 93:2260-2263.
Asseman, C., S. Mauze, M. W. Leach, R. L. Coffman, and F. Powrie. 1999. An essential role for IL-10 in the function of regulatory T cells that inhibit intestinal inflammation. *J. Exp. Med* 190:995-1004.
Bach, J.F. 1994. Insulin-dependent diabetes mellitus as an autoimmune disease. *Endroc. Rev.* 15:516-542.
Balasa, B., and N. Sarvetnick. 1996. The paradoxical effects of interleukin 10 in the immunoregulation of autoimmune diabetes. *Autoimmun.* 9:283-286.
Barrat, F.J., D.J. Cua, A. Boonstra, D.F. Richards, C. Crain, H.F. Savelkoul, R. de WaalMalefyt, R.L. Coffman, C.M. Hawrylowicz, and A. O'Garra. 2002. In vitro generation of interleukin 10-producing regulatory CD4+ T cells is induced by immunosuppressive drugs and inhibited by T helper type 1 (Th1)- and Th2-inducing cytokines. *J Exp. Med.* 195:603-616.
Bonifacio, E., M. Atkinson, G. Eisenbarth, D. Serreze, T.W. Kay, E. Lee-Chan, and B. Singh. 2001. International workshop on lessons from animal models for human type 1 diabetes: identification of insulin but not glutamic acid decarboxylase or IA-2 as specific autoantigens of humoral autoimmunity in nonobese diabetic mice. *Diabetes*. 50:2451-2458.
Bot, A., D. Smith, S. Bot, A. Hughes, T. Wolfe, L. Wang, C. Woods, and M. von Herrath. 2001. Plasmid vaccination with insulin B chain prevents autoimmune diabetes in nonobese diabetic mice. *J. Immunol.* 176: 2950-2955.
Brumeanu, T.D., W.J. Swiggard, R.M. Steinman, C.A. Bona, and H. Zaghouani. 1993. Efficient loading of identical viral peptide onto class II molecules by antigenized immunoglobulin and influenza virus. *J. Exp. Med.* 178:1795-1799.
Buschard, K., T. Bock, C.R. Pederson, S.V. Hansen, K. Aaen, M. Jorgenson, M.W. Hansen, T.W. Kjaer, I. Hageman, and K. Josefsen. 2000. Neonatal treatment with beta-cell stimulatory agents reduces the incidence of diabetes in BB rats. *Int. Exp. Diabetes Res.* 1:1-8.
Castano, L., and G.S. Eisenbarth. 1990. Type-1 diabetes: a chronic autoimmune disease of human, mouse, and rat. *Ann Rev. Immunol.* 8:647-680.
Christen, U., T. Wolfe, U. MOhrle, A.C. Hughes, E. Rodrigo, E.A. Green, R.A. Flavell, and M.G. von Herrath. 2001. A dual role for TNF-a in type I diabetes: islet-specific expression abrogates the ongoing autoimmune process when induced late but not early during pathogenesis. *J. Immunol.* 166:7023-7032.
Christian, C.L. 1960. Studies on aggregated gamma-globulin I & II. *J Immunol.* 84:112-121.
Daniel, D., and D.R. Wegmann. 1996. Protection of nonobese diabetic mice from diabetes by intranasal or subcutaneous administration of insulin peptide B (9-23). *Proc. Natl. Acad. Sci. USA*. 93:956-960.
Delovitch, T., and B. Singh. 1997. The nonobese diabetic mouse as a model of autoimmune diabetes: immune dysregulation gets the NOD. *Immunity*. 7:727-738.
Dotta, Francesco, Marcello Previti, Marguerite Neerman-Arbez, Sabrina Dionisi, Domenico Cucinotta, Luisa Lenti, Umberto DiMario, The GM2-1 Ganglioside Islet Autoantigen in Insulin-Dependent Diabetes Mellitus is Expressed in Secretory Grnaules and is Not β-Cell Specific, *Endocrinology*, 139(1):316-319, 1998.
Faveeuw, C., M.C. Gagnerault, and F. Lepault. 1995. Isolation of leukocytes infiltrating the islets of Langerhans of diabetes-prone mice for flow cytometric analysis. *J. Immunol. Methods*. 187:163-169.
Gottlieb, P.A., and G.S. Eisenbarth. 2002. Insulin-specific tolerance in diabetes. *Clin. Immunol.* 102:2-11.
Groux, H., A. O'Garra, M. Bigler, M. Rouleau, J. de Vries, and M.-G. Roncarolo. 1997. Generation of a novel regulatory CD4+ T-cell population, which inhibits antigen-specific T-cell responses. *Nature*. 389:737-742.

Heath, V.L., P. Hutchings, D.J. Fowell, A. Cooke, and D. Mason. 1999. Peptides derived from murine insulin are diabetogenic in both rats and mice, but the disease-inducing epitopes are different: evidence against a common environmental cross-reactivity in the pathogenicity of type I diabetes. *Diabetes*. 48:2157-2165.
Honeyman, Margo C, Natalie L. Stone, and Leonard C. Harrison, T-Cell Epitopes in Type 1 Diabetes Autoantigen Tyrosin Phosphatase LA-2: Potential for Mimicry with Rotavirus and Other Environmental Agents, *Molecular Medicine*, 4:231-239, 1998.
Jun, H.S., Y.H. Chung, J. Han, A. Kim, S.S. Yoo, R.S. Sherwin, and Yoon, J.W. (2002). H.S. Jun et al.: Prevention of autoimmune diabetes by GAD imunogene therapy. *Diabetologia*. 45:668-676.
Latek, R.R., A. Sufi, S.J. Petzold, C.A. Nelson, 0. Kanagawa, E.R. Unanue, and D.H. Fremont. 2000. Structural basis of peptide binding and presentation by the type 1 diabetes-associated MHC class II molecule of NOD mice. *Immunity*. 12:699-710.
Lee, M.-S., R. Mueller, L. Wicker, L.B. Peterson, and N. Sarvetnick. 1996. IL-10 is necessary and sufficient for autoimmune diabetes in conjunction with NOD MHC homozygosity. *J. Exp. Med.* 183:2663-2668.
Legge, K.L., B. Min, N.T. Potter, and H. Zaghouani. 1997. Presentation of a T cell receptor antagonist peptide by immunoglobulins ablates activation of T cells by a synthetic peptide or proteins requiring endocytic processing. *Exp. Med.* 185:1043-1053.
Legge, K.L., R.K. Gregg, R. Maldonado-Lopez, L. Li, J.C. Caprio, M. Moser, and H. Zaghouani. 2002. On the role of dendritic cells in peripheral T cell tolerance and modulation of autoimmunity. *Exp. Med*. 196:217-227.
Liblau, R.S., S.M. Singer, and H.O. McDevitt. 1995. Th1 and Th2 CD4+ T cells in the pathogenesis of organ-specific autoimmune diseases. *Immunol. Today*. 16:34-37.
Liu, C. Detection of Glutamic Acid Decarboxylase-Activated T cells with I-Ag7 Tetramers. PNAS. 97(26): 14596-14601, 2000.
Makino, S., K. Kunimoto, Y. Muraoka, Y. Mizushima, K. Katagiri, and Y. Tochino. 1980. Breeding of a non-obese, diabetic strain of mice. *Jikken Dobutsu*. 29:1-13.
Min, B., K.L. Legge, C. Pack, and H. Zaghouani. 1998. Neonatal exposure to a selfpeptide-immunoglobulin chimera circumvents the use of adjuvant and confers resistance to autoimmune disease by a novel mechanism involving interleukin 4 lymph node deviation and interferon y-mediated splenic anergy. *J. Exp. Med.* 188:2007-2017.
Moritani, M., K. Yoshimoto, S. Ii, M. Kondo, H. Iwahana, T. Yamaoka, T. Sano, N. Nakano, H. Kikutani, and M. Itakura. Prevention of adoptively transferred diabetes in nonobese diabetic mice with IL-10-transduced islet-specific Th1 lymphocytes. *J. Clin. Invest*. 98:1851-1859.
Pennline, K.J., E. Roque-Gaffney, and M. Monahan. 1994. Recombinant human IL-10 prevents the onset of diabetes in the nonobese diabetic mouse. *Clin. Immunol. Immunopathol*. 71:169-175.
Phillips, J.M., N.M. Parish, M. Drage, and A. Cooke. 2001. Cutting edge: interactions through the IL-10 receptor regulate autoimmune diabetes. *J. Immunol*. 167:6087-6091.
Pietropaolo, Massimo, Luis Castano, Sunanda Babu, Roland Buelow, Yu-Ling S. Kuo, Stephan Martin, Andrea Martin, Alvin C. Powers, Michal Prochazka, Jurgen Naggert, Edward H. Leiter, and George S. Eisenbarth, Islet Cell Autoantigen 69 kD (ICA69): Molecular Cloning and Characterization of a Novel Diabetes-Associated Autoantigen, *J. Clin. Invest.*, 92:359-371, Jul. 1993.
Quintana, F.J., A. Rotem, P. Carmi, and I.R. Cohen. 2000. Vaccination with empty plasmid DNA or CpG oligonucleotide inhibits diabetes in nonobese diabetic mince: modulation of spontaneous 60-kDa heat shock protein autoimmunity.*J. Immunol*. 16:148-155.
Roep, Bart O, Perspectives in Diabetes: T-Cell Responses to Autoantigens in IDDM: The Search for the Holy Grail. *Diabetes*, 45:1147-1156, Sep. 1996.
Romani, N., N. Bhardwaj, M. Pope, F. Koch, W.J. Swigard, U.O. Doherty, M.D. Witmer-Pack, L. Hoffman, G. Schuler, K. Inaba, and R.M. Steinman. 1996. Dendritic cells. In Weirs Handbook of Experimental Immunology. L.A. Herzenberg, D. Weir, and C. Blackwell, editors. Blackwell Science, Cambridge. 156.1-156.14.
Roncarolo, M.G., R. Bacchetta, C. Bordignon, S. Narula, and M.K. Levings. 2001. Type 1 T regulatory cells. *Immunol. Rev*. 182:68-79.

(56) References Cited

OTHER PUBLICATIONS

Rosenqvist, E., T. Jossang, and J. Feder. 1987. Thermal properties of human IgG. *Mol. Immunol.* 24:495-501.

Sarvetnick, N., J. Shizuru, D. Liggitt, L. Martin, B. McIntyre, A. Gregory, T. Parslow, and T.A. Stewart. 1990. Loss of pancreatic islet tolerance induced by 13-cell expression of interferon-y. *Nature.* 346:844-847.

Serreze, D.V., H.D. Chapman, C.M. Post, E.A. Johnson, W.L. Suarez-Pinzon, and A. Rabinovitch. 2001. Th1 to Th2 cytokine shifts in nonobese diabetic mice: sometimes an outcome, rather than the cause of diabetes resistance elicited by immunostimulation. *J. Immunol.* 166:1352-1359.

Shevach, E. M. 2000. Regulatory T cell in autoimmunity. *Ann. Rev. Immunol.* 18: 423-450.

Song, H.Y., M.M. Abad, C.P. Mahoney, and R.C. McEnvoy. 1999. Human insulin B chain but not A chain decreases the rate of diabetes in BB rats. *Diabetes Res. Clin. Pract.* 46:109-114.

Tisch, R., and H.O. McDevitt. 1996. Insulin dependent diabetes mellitus. *Cell.* 85:291-297.

Wang, B., I. Andre, A. Gonzalez, J. Katz, M. Aguet, C. Benoist, and D. Mathis. 1997. Interferon-y impacts at multiple points during the progression of autoimmune diabetes. *Proc. Natl. Acad. Sci. USA.* 94:13844-13849.

Wegmann, D.R., M. Norbury-Glaser, and D. Daniel. 1994. Insulin-specific T cells are a predominant component of islet infiltrates in pre-diabetic NOD mice. *Eur. I Immunol.* 24:1853-1857.

Wogensen, L., M.-S. Lee, and N. Sarvetnick. 1994. Production of interleukin 10 by islet cells accelerates immune-mediated destruction of 13 cells in nonobese diabetic mice. *Exp. Med.* 179:1379-1384.

Yang, Z., M. Chen, R. Wu, L.B. Fialkow, J.S. Bromber, M. McDuffie, A. Naji, and J. Nadler. 2002. Suppression of autoimmune diabetes by viral IL-10 gene transfer *J. Immunol.* 168:6479-6485.

Yu, L., D.T. Robles, N. Abiru, P. Kaur, M. Rewers, K. Kelemen, and G.S. Eisenbarth. 2000. Early expression of antiinsulin autoantibodies of humans and the NOD mouse: evidence for early determination of subsequent diabetes. *Proc. Natl. Acad. Sci. USA.* 97:1701-1706.

Zaghouani, H., R. Steinman, R. Nonacs, H. Shah, W. Gerhard, and C. Bona. 1993. Presentation of a viral T cell epitope expressed in the CDR3 region of a self immunoglobulin molecule. *Science.* 259:224-227.

Zheng, X., A. Steele, W. Hancock, A.C. Stevens, P.W. Nickerson, P. Roy-Chaudhury, Y. Tian, and T.B. Strom. 1997. A noncytolytic IL-10/Fc fusion protein prevents diabetes, blocks autoimmunity, and promotes suppressor phenomena in NOD mice../. *Immunol.* 158:45074513.

\* cited by examiner

Figure 1 Gregg, R.K., et al.

Figur 9

METHOD FOR ENDOCYTIC PRESENTATION OF AN IMMUNOSUPPRESSIVE FOR THE TREATMENT OF TYPE 1 DIABETES

This application is a continuation-in-part of International Patent Application No. PCT/US03/10700, filed Apr. 8, 2003, which claims priority to U.S. Provisional Patent Application Ser. No. 60/371,663, filed Apr. 9, 2002, the entirety of both of which are hereby incorporated by reference herein.

FIELD OF THE INVENTION

The present invention relates generally to methods, compounds, compositions, combinations, and kits for treating, preventing, suppressing, or delaying the onset of, or reducing the risk of developing type 1 diabetes, or the symptoms associated with, or related to, type 1 diabetes, in a subject in need thereof. In one aspect, the invention relates to the use of compounds, compositions, combinations, kits, and methods for endocytic presentation of an immunosuppressive factor for the down regulation of diabetogenic T cells for the treatment of type 1 diabetes before and/or after the expression of predisposition markers.

BACKGROUND OF THE INVENTION

Type 1 diabetes, also known as insulin-dependent diabetes mellitus ("IDDM"), is an autoimmune disease in which the beta ("β") cells of the pancreatic islets of Langerhans are destroyed as a consequence of inflammatory reactions triggered by activation of T cells specific for β-cell associated antigens (1, 2; see "Reference" section at the end of the document). Data obtained from preclinical animal models of IDDM as well as clinical studies have implicated $CD4^+$ and $CD8^+$ autoreactive T cells as key effectors of islet cell destruction (J. F. Bach, Endocr. Rev., 1994). Despite the availability of insulin replacement therapy to maintain acceptable control of blood glucose levels, chronic insulin replacement therapy is still associated with major side effects including potential for acute hypoglycemia, chronic microvascular disease (retinopathy, nephropathy and neuropathy) and chronic macrovascular disease (heart disease and stroke) all resulting from the poor fine control of carbohydrate metabolism that can be attained with bolus injection of insulin (Simone et al., Diabetes Care, 22 Suppl. 2.: B7-B 15, 1999). These side effects, combined with the high cost, the invasive nature of insulin therapy and the increasing prevalence of IDDM in the developed world, have led to efforts for finding alternative strategies including methods of preventing progression from the inciting autoreactive process to the irreversible loss of over 90% of the islet mass that correlates with clinical presentation of disease.

The non-obese diabetic ("NOD") mouse develops a spontaneous type 1 diabetes that shares many of the features associated with human IDDM providing a well characterized animal model for this complex autoimmune disease (3). The initial or pre-insulitis stage of disease begins around 3 weeks of age and involves cell infiltration in areas surrounding the pancreatic islets without damage of the β cells (4). The next phase of disease, known as insulitis, begins around the age of 6 weeks and involves a gradual increase in cell infiltration which ultimately overcomes the immunoregulatory mechanisms in place leading to a progressive destruction of the β cells (5). Complete loss of insulin production leads to dysregulation of glucose metabolism and overt diabetes can manifest as early as 12 weeks of age (6). It is now well accepted that progression from insulitis to diabetes correlates with a rise of Th1 type cells specific for n-cell associated antigens (7). Cytokines such as IFNγ and TNFα produced by these Th1 cells stimulate recruitment of inflammatory cells capable of β cell destruction (8-10). Hence, down-regulation of the Th1 cells would be a logical approach to combat diabetes. A number of antigen-specific strategies are being considered for modulation of the autoreactive T cells and met with success in NOD mice (11-14) as well as other animal models of IDDM (15, 16). The translation to human, however, is not yet in place and issues such as practicality, side effects, and efficacy have to be overcome in order for the transition to occur.

Recently, it has been have shown that delivery of class II-restricted peptides on immunoglobulins ("Igs") increases presentation to T cells by 100-fold relative to free peptide (17, 18). This is due to internalization of Igs via Fcγ receptors ("FcγR") processing within the endosomal compartment and unlimited access of the peptides to newly synthesized MHC molecules (19). Given the fact that Igs are self-molecules, side effects are minimal even when repetitive injections are required. Furthermore, due to their autologous nature, when injected into animals without adjuvant, Igs do not induce inflammatory signals that up-regulate costimulatory molecules on antigen presenting cells ("APCs") (20). Indeed, adjuvant-free regimens that used Igs to vehicle antigenic peptides have proven effective for induction of tolerance rather than immunity (20-23). For instance, when PLP1 peptide, corresponding to the encephalitogenic sequence 139-151 of proteolipid protein ("PLP"), was expressed on an Ig molecule, the resulting Ig-PLP1 displayed modulatory functions against experimental allergic encephalomyelitis ("EAE") and suppressed paralytic relapses (20, 22). Furthermore, aggregation of Ig-PLP1 led to cross-linking of FcγR and induction of IL-10 production by the presenting APCs (20, 22). Consequently, aggregated ("agg") Ig-PLP1 displayed a greater potency against EAE inducing full and expeditious recovery from disease suppressing both the initial severe paralytic phase and the relapses (22). Neutralization of IL-10 by injection of anti-IL-10 antibody reversed the course of action of agg Ig-PLP1 and the disease rebounded indicating that endogenous IL-10 plays a critical role in the prevention of autoimmunity. Moreover, the Ig delivery approach proved effective with a myelin oligodendrocyte glycoprotein ("MOG") peptide and Ig-MOG was able to suppress EAE even when disease induction used central nervous system ("CNS") homogenate which includes multiple epitopes (23). The conclusion that has been drawn from these observations demonstrates that agg Ig chimeras couple endogenous IL-10 to peripheral tolerance setting into motion a multi-modal approach effective against complex autoimmunity involving diverse T cell specificities (20, 22, 23). In the NOD system, IL-10 has been shown to display variable effects on diabetes depending upon the mode of delivery (24-26) and the age of the animal (27-29). Apart from this variable function, the lack of a practical delivery strategy and the ill-defined mechanism underlying the mode of action of IL-10 justifies the search for new approaches to direct endogenous IL-10 against diverse diabetogenic T cells and prevent spontaneous diabetes in the NOD mouse.

Therefore, there is a need for additional treatment regimes for the treatment, and/or prevention, and/or reduction in the risk of developing type 1 diabetes, or the symptoms associated with, or related to, type 1 diabetes, in a subject in need thereof. The discussion that follows discloses methods, compounds, compositions, combinations, and kits that help to fulfill these needs.

SUMMARY OF THE INVENTION

The present invention is directed to methods, compounds, compositions, combinations, and kits for treating, preventing, suppressing or delaying the onset, or reducing the risk of developing type 1 diabetes, or the symptoms associated with, or related to, type 1 diabetes, in a subject in need thereof. In one aspect, the present invention is directed to compounds, compositions, kits, and methods for endocytic presentation of an immunosuppressive factor for the down regulation of diabetogenic T cells for the treatment or prevention of type 1 diabetes. In yet another embodiment of the present invention, methods, kits, combinations, and compositions containing at least one immunoglobulin, for example, INS, GAD, an insulin protein, a peptide derived from insulin, a diabetogenic epitope, or a T cell receptor engaging determinant, are provided to treat, prevent, suppress, or delay the onset of type 1 diabetes after expression of an IAA predisposition marker.

The present invention also provides a method for the treatment or prevention of type 1 diabetes in a subject in need thereof. In one embodiment, the treatment or prevention is during the pre-insulitis stage of diabetes. In yet another embodiment, the subject has not yet undergone IAA seroconversion. In one embodiment, the treatment or prevention is before and/or after the expression of predisposition markers. In yet another embodiment, the subject may or may not have progressed to a hyperglycemic stage. The method comprises administering to the subject a composition that comprises an immunoglobulin, or portion thereof, linked to a peptide wherein the immunoglobulin or portion thereof is aggregated.

The present invention also provides a method for the treatment or prevention of the symptoms associated with, or related to, type 1 diabetes in a subject in need thereof. In one embodiment, the treatment or prevention of the symptoms is during the pre-insulitis stage of diabetes. In yet another embodiment, the subject has not yet undergone IAA seroconversion. The method comprises administering to the subject a composition that comprises an immunoglobulin, or portion thereof, linked to a peptide wherein the immunoglobulin or portion thereof is aggregated.

In another embodiment of the present invention, the methods, compounds, compositions, combinations, and kits are directed to treating, preventing or reducing the risk of developing type 1 diabetes in an at-risk patient expressing a predisposition marker.

The present invention also provides a composition comprising an immunoglobulin, or portion thereof, linked to a protein fragment or peptide wherein the immunoglobulin, or portion thereof, is capable of binding to an Fc receptor. In one embodiment of the present invention, the peptide is derived from INS and/or GAD, such as, for example, INSβ, GAD 1 and GAD2. In yet another embodiment, the composition has the property of being endocytosed by cells bearing the Fc receptor and processed and presented by the cells to present the peptide to endogenous MHC Class II molecules, thereby substantially reducing or preventing activation of diabetogenic T cells specific for the peptide.

The present invention is also directed to methods, combinations and kits, where the composition of the method, combination or kit comprises an immunoglobulin or portion thereof linked to one or more peptides wherein the immunoglobulin, or portion thereof, and is capable of binding to an Fc receptor and being endocytosed by an antigen presenting cell. In one embodiment, the one or more peptides or fragments thereof provides a T cell receptor antagonist for presentation on the surface of the antigen presenting cell upon endocytic processing for the preparation of a pharmaceutical composition for alleviating symptoms associates with type 1 diabetes for a subject in need.

A method for presenting T cell receptor engaging determinant or epitope on the surface of a professional or nonprofessional antigen presenting cell is also provided by the present invention.

The present invention is also directed to methods of treating a disease, condition or disorder by administering a pharmaceutical composition of the present invention where treatment with an anti-diabetic type I agent is indicated.

Illustratively, various non-limiting embodiments of the invention include:

1) A method for the treatment of type 1 diabetes in a patient during the pre-insulitis stage of diabetes by administration of a composition comprising an immunoglobulin or portion thereof linked to a peptide wherein the immunoglobulin or portion thereof is aggregated.
2) The method of paragraph 1 wherein the patient has not yet undergone IAA seroconversion.
3) The method of paragraphs 1 and 2 wherein the aggregated immunoglobulin or portion thereof is capable of binding to an Fc receptor and the peptide is presented to T cells in association with MHC class II molecules.
4) The method of paragraph 3 wherein the T cells are specific for the peptide.
5) The method of paragraphs 3 and 4 wherein the peptide is a T cell receptor engaging determinant.
6) The method of paragraph 1 wherein the composition is endocytosed by cells having an Fc receptor and is processed and presented by the cells in association with MHC class II molecules thereby substantially reducing or preventing activation of diabetogenic T cells.
7) The method of paragraphs 1-6 wherein the peptide contains a diabetogenic epitope.
8) The method of paragraph 1 wherein the peptide is the INSβ peptide.
9) The method of paragraph 1 and 6 wherein the peptide is derived from insulin.
10) The method of paragraph 1 wherein the composition enhances IL-10 production in splenic T cells.
11) The method of paragraph 1, 8 and 10 wherein administering of the composition delays the onset of type 1 diabetes.
12) The method of paragraph 3 wherein the receptor is an Fcγ receptor.
13) The method of paragraph 12 wherein the aggregated Ig-INSβ compositions cross-link Fcγ receptors.
14) The method of paragraph 1 wherein the composition induces production of IL-10.
15) The method of paragraph 14 wherein the composition induces production of IL-10 by APCs thereby enhancing peripheral tolerance to the onset of diabetes at the pre-insulitic stage.
16) The method of paragraph 1 wherein the composition induces production of TGFβ and IL-10 producing T cells.
17) The method of paragraph 16 wherein the T cells are nonproliferative antigen specific T cells.
18) The method of paragraphs 1 and 8 wherein the peptide is inserted within the variable region of the immunoglobulin or portion thereof and the immunoglobulin or portion thereof comprises human IgG or humanized IgG.
19) The method of paragraph 18 wherein the peptide is inserted within variable region of the immunoglobulin or portion thereof selected from the group consisting of the CDR1, CDR2 and CDR3 region.

20) The method of paragraphs 1 and 18 wherein the peptide is inserted with CDR3 region of the immunoglobulin or portion thereof by deleting the D segment and insertion of the peptide.
21) The method of paragraph 1 wherein the peptide is selected from the group consisting of GAD1 and GAD2.
22) The method of paragraph 1 wherein the composition is selected from the group consisting of IgINS (peptides derived from human insulin), IgGAD (peptides derived from GAD), IgINSβ, IgGAD1 and IgGAD2.
23) A method of treatment of type 1 diabetes in an at-risk patient expressing a predisposition marker with a composition comprising an immunoglobulin or portion thereof linked to a diabetogenic peptide wherein the composition is soluble.
24) The method of paragraph 23 wherein the patient is in the pre-insulitis stage of type 1 diabetes.
25) The method of paragraph 23 wherein the patient is expressing predisposition markers IAA positive or GAD positive.
26) The method of paragraph 23 wherein the patient expresses a predisposition marker but has not progressed to a hyperglycemic stage.
27) The method of paragraphs 23-26 wherein the composition consists of soluble Ig-INSβ.
28) The method of paragraphs 23-26 wherein the composition is effective in delaying the onset of type 1 diabetes in the patient at the pre-insulitis stage or following seroconversion.
29) The method of paragraphs 23-26 wherein the soluble Ig-INSβ is administered weekly and achieves full suppression of type 1 diabetes.
30) The method of paragraph 23 wherein the composition is selected from the group consisting of Ig-INSβ, Ig-GAD1, IgGAD2 or an immunoglobulin or a portion thereof linked to a peptide derived from GAD65.
31) The method of paragraphs 23-26 wherein the composition is endocytosed by cells having an Fc receptor and is processed and presented by the cells in association with MHC class II molecules thereby substantially reducing or preventing activation of diabetogenic T cells.
32) The method of paragraph 31 wherein the T cells are antigen specific.
33) A composition comprising an immunoglobulin or portion thereof linked to a protein fragment or peptide wherein the immunoglobulin or portion thereof is capable of binding to an Fc receptor, the peptide being selected from the group consisting of peptides derived from INS and GAD and more specifically INSβ, GAD 1 and GAD2, the composition having the property of being endocytosed by cells bearing the Fc receptor and processed and presented by the cells to present the peptide to endogenous MI-IC Class II molecules, thereby substantially reducing or preventing activation of diabetogenic T cells specific for the peptide.
34) The composition of paragraph 33 wherein the composition is selected from the group consisting of agg Ig-INSβ and soluble Ig-INSβ.
35) The composition of paragraph 33 wherein the peptide is a T cell receptor engaging determinant.
36) The composition of paragraphs 33 and 34 wherein the peptide is inserted within the variable region of the immunoglobulin or portion thereof.
37) The composition of paragraphs 33-36 wherein the peptide is inserted within the region selected from the group consisting of CDR1, CDR2 and CDR3.
38) The composition of paragraphs 33 and 34 wherein the immunoglobulin or portion thereof is human IgG or derived from human IgG or humanized IgG.
39) The composition of paragraph 33 wherein the immunoglobulin or portion thereof is in an aggregated form.
40) The composition of paragraph 33 wherein the composition is in soluble form.
41) The composition of paragraphs 33 and 34 wherein the composition further comprises a pharmaceutically acceptable carrier.
42) Use of a composition wherein the composition comprises an immunoglobulin or portion thereof linked to one or more peptides wherein the immunoglobulin or portion thereof is capable of binding to an Fc receptor and being endocytosed by an antigen presenting cell and the one or more peptides or fragments thereof provide one or more T cell receptor antagonists for presentation on the surface of the antigen presenting cell upon endocytic processing for the preparation of a pharmaceutical composition for alleviating symptoms associates with type 1 diabetes for a patient in need.
43) The use of paragraph 42 wherein the one or more peptides is selected from the group consisting of INSβ, GAD-1 and GAD-2.
44) The use of paragraph 41 wherein the composition is selected from the group consisting of Ig-INSβ, Ig-GAD1 and Ig-GAD2.
45) The use of paragraphs 42-44 wherein the composition further comprises a pharmaceutically acceptable carrier.
46) The use of paragraphs 42-44 wherein the immunoglobulin or portion thereof is comprised of at least part of a domain of a constant region of an immunoglobulin.
47) The use of paragraphs 42-44 wherein the immunoglobulin or portion thereof comprises human IgG or a portion thereof.
48) The use of paragraphs 42-47 wherein the immunoglobulin or portion thereof is aggregated.
49) The use of paragraphs 42-47 wherein the composition is soluble.
50) A method for presenting T cell receptor engaging determinant or epitope on the surface of a professional or nonprofessional antigen presenting cell comprising the steps of:
   a) providing a composition wherein the composition comprises an immunoglobulin or portion thereof linked to one or more peptides wherein the immunoglobulin or portion thereof is capable of binding to an Fc receptor and being endocytosed by an antigen presenting cell and the one or more peptides or fragments thereof provide one or more T cell receptor engaging determinants or epitopes for presentation on the surface of the antigen presenting cell upon endocytic processing;
   b) contacting the composition with at least one Fc receptor present on a surface of a professional or nonprofessional antigen presenting cell whereby the composition is internalized by the antigen presenting cell; and
   c) endocytically processing the internalized composition to provide one or more T cell receptor engaging determinants or epitopes wherein the one or more provided T cell receptor engaging determinants or epitopes are presented on the surface of the antigen presenting cell.
51) The method of paragraph 49 wherein the one or more provided T cell receptor engaging determinants or epitopes is presented on the surface of the antigen presenting cells associated with at least on MHC complex.
52) The method of paragraph 50 wherein the MHC complex is the MHC Class II molecule.

53) The method of paragraphs 49-52 wherein the peptides are selected from the group consisting of peptides derived from insulin and GAD and specifically INSβ, GAD-1 and GAD-2.

54) The method of paragraphs 49-51 wherein the composition is selected from the group consisting of Ig-INSβ, Ig-GAD1 and Ig-GAD2.

55) A method of suspending the onset of type 1 diabetes in a subject that has undergone IAA seroconversion, the method comprising administering to the subject a pharmaceutically acceptable composition comprising at least one immunoglobulin selected from the group consisting of INS, GAD, an insulin protein, a peptide derived from insulin, a diabetogenic epitope, and a T cell receptor engaging determinant; wherein the composition is administered to the subject in one or more dosage administrations.

56) The method of paragraph 55, wherein the immunoglobulin is human or humanized.

57) The method of paragraphs 55-56, wherein the subject is a human subject.

58) The method of paragraphs 55-57, wherein the administration of the composition to the subject results in down regulation of an autoreactive T cell.

59) The method of paragraphs 55-58, wherein a peptide is inserted within a variable region of the immunoglobulin.

60) The method of paragraph 59, wherein the variable region of the immunoglobulin comprises a CDR1, a CDR2, or a CDR3 region.

61) The method of paragraphs 59-60, wherein activation of an autoreactive T cell specific for the peptide is substantially reduced or prevented.

62) The method of paragraph 55, wherein the INS comprises INSβ.

63) The method of paragraph 62, wherein the INSβ is soluble.

64) The method of paragraph 63, wherein the soluble INSβ is capable of binding to at least one Fc receptor.

65) The method of paragraph 64, wherein the Fc receptor is a Fcγ receptor.

66) The method of paragraph 64, wherein the composition is endocytosed by antigen presenting cells.

67) The method of paragraphs 55-66, wherein the GAD comprises GAD 1, GAD2, or GAD65.

68) The method of paragraphs 55-67, wherein the subject is IAA-positive.

69) The method of paragraphs 55-68, wherein the subject is GAD positive.

70) The method of paragraphs 55-69, wherein the subject has not developed hyperglycemia.

71) The method of paragraphs 55-70, wherein the subject expresses a type 1 diabetes predisposition marker.

72) The method of paragraphs 55-71, wherein upon administration of the composition to the subject, the subject undergoes a dose dependent delay in the onset of type 1 diabetes.

73) The method of paragraphs 55-72, wherein the administration of the composition occurs before the type-1 diabetes progresses to an irreversible stage.

74) The method of paragraphs 55-73, wherein the composition is formulated as an injectable formulation.

75) The method of paragraphs 55-74, wherein the injectable formulation comprises an aqueous solution or suspension.

76) The method of paragraph 75, wherein the composition is administered by an injection or an infusion.

77) The method of paragraph 76, wherein the composition is administered by intra-venous infusion.

78) The method of paragraphs 55-77, wherein the composition further comprises at least one pharmaceutically acceptable carrier.

79) The method of paragraphs 55-78, wherein the one or more dosage administrations are provided to the subject on a continuous, hourly, daily, bi-weekly, weekly, or monthly basis for a period of time sufficient to substantially delay the onset of the type 1 diabetes.

80) The method of paragraph 79, wherein the period of time is adequate to substantially reduce or prevent the development of hyperglycemia in the subject.

81) The method of paragraph 79, wherein the composition is administered to the subject within about one week after determining that the subject has undergone IAA seroconversion.

82) The method of paragraph 79, wherein the composition is administered to the subject within about one month after determining that the subject has undergone IAA seroconversion.

83) The method of paragraphs 55-82, wherein at least one of the one or more dosage administrations comprise a first dosage administration followed by an administration of one or more additional dosage administrations.

84) The method of paragraph 83, wherein at least one of the one or more additional dosage administrations is within about a month of the first dosage administration.

85) The method of paragraph 83, wherein at least one of the one or more additional dosage administrations is within about a week of the first dosage administration.

86) The method of paragraph 83, wherein the one or more additional dosage administrations is within about a day of the first dosage administration.

87) The method of paragraph 83, wherein the one or more additional dosage administrations is administered to the subject on a continuous, hourly, daily, bi-weekly, weekly, or monthly basis.

88) The method of paragraph 83, wherein at least one of the one or more additional dosage administrations is administered to the subject at least about 1 week after the administration of the first dosage administration.

89) The method of paragraph 83, wherein at least one of the one or more additional dosage administrations is administered to the subject at least about 1 month after the administration of the first dosage administration.

90) The method of paragraph 83, wherein at least one of the one or more additional dosage administrations is administered to the subject at least about 6 months after the administration of the first dosage administration.

91) The method of paragraphs 55-90, wherein the one or more additional dosage administrations is administered in a plurality of dosage administrations administered at substantially equal time intervals throughout the time period.

92) The method of paragraphs 55-91, wherein the composition is administered to the subject in an amount sufficient to provide the soluble Ig-INSβ in an amount of not less than about 0.001 mg/kg body weight of the subject per day.

93) The method of paragraphs 55-92, wherein the composition is administered to the subject in an amount sufficient to provide the soluble Ig-INSβ in an amount of not less than about 0.01 mg/kg body weight of the subject per day.

94) The method of paragraphs 55-93, wherein the composition is administered to the subject in an amount sufficient to provide the soluble Ig-INSβ in an amount of not less than about 0.05 mg/kg body weight of the subject per day.

95) A composition for suppressing the onset of type 1 diabetes in a subject that has undergone IAA seroconversion, the composition comprises: a pharmaceutically acceptable composition comprising at least one immunoglobulin selected from the group consisting of INS, GAD, an insulin protein, a peptide derived from insulin, a diabetogenic epitope, and a T cell receptor engaging determinant.

96) A method of use a composition according to paragraph 95 in the manufacture of a medicament for delaying the onset of type 1 diabetes in a subject that has undergone IAA seroconversion.

97) A kit for delaying the onset of type 1 diabetes in a subject that has undergone IAA seroconversion, the kit comprises: a pharmaceutically acceptable composition comprising at least one immunoglobulin selected from the group consisting of INS, GAD, an insulin protein, a peptide derived from insulin, a diabetogenic epitope, and a T cell receptor engaging determinant.

BRIEF DESCRIPTION OF THE DRAWINGS

Other advantages of the present invention will be readily appreciated as the same becomes better understood by reference to the following detailed description when considered in connection with the accompanying drawing wherein:

FIGS. 2(c) and 2(d) indicate that presentation of INSβ and Ig-INSβ is specific;

DETAILED DESCRIPTION OF THE INVENTION

Figure 1:
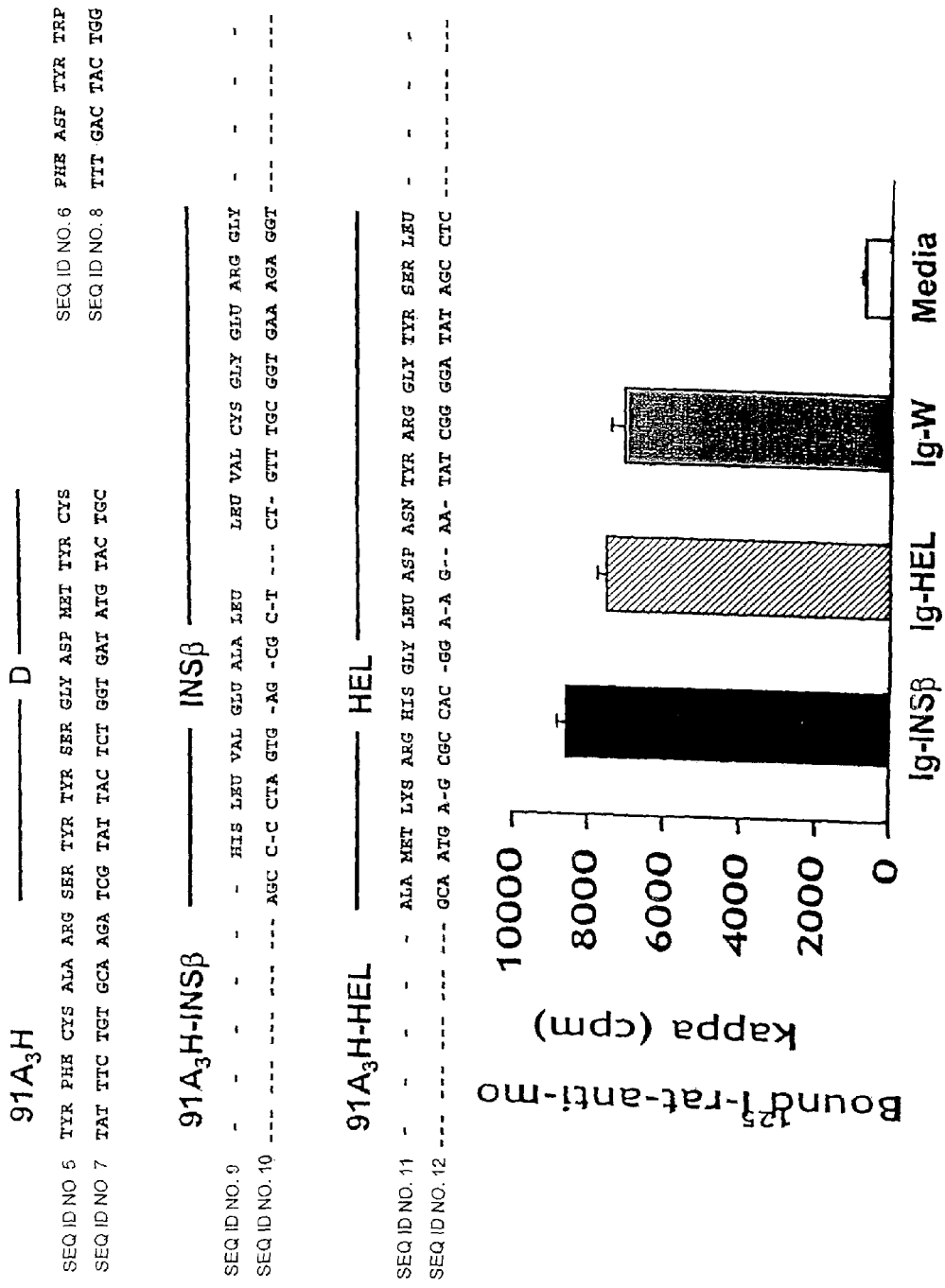
FIG. 1 shows the nucleotide and amino acid sequences of the INSβ (SEQ ID NO: 5 and SEQ ID NO: 6, respectively) and HEL (SEQ ID NO: 7 and SEQ ID NO: 8, respectively) inserts as well as flanking regions surrounding them within the heavy chain CDR3 of the 91A3 Ig (SEQ ID NO: 9, SEQ ID NO: 10, SEQ ID NO: 11 and SEQ ID NO: 12). The lower panel of FIG. 1 shows secreted chimeric Ig in the supernatant from transfected cells indicating that complete constructs were created.

The present invention is directed to methods, kits, combinations, and compositions for treating, preventing, suppressing or delaying the onset of a disease, condition or disorder where treatment with an anti-diabetic type 1 agent is indicated.

It has been discovered that a composition comprising an immunosuppressive factor for the down regulation of diabetogenic T cells for endocytic presentation are unique compositions exhibiting superior performance for the treatment of type 1 diabetes.

It has also been discovered that a composition comprising at least one immunoglobulin, for example, INS, GAD, an insulin protein, a peptide derived from insulin, a diabetogenic epitope, or a T cell receptor engaging determinant are unique compositions exhibiting superior performance for the treatment, prevention, suppression or delaying of the onset of a disease type 1 diabetes.

While the present invention may be embodied in many different forms, several specific embodiments are discussed herein with the understanding that the present disclosure is to be considered only as an exemplification of the principles of the invention, and it is not intended to limit the invention to the embodiments illustrated. For example, where the invention is illustrated herein with particular reference to Ig-INSβ, it will be understood that any other immunoglobulin, such as Ig-CAD-1 or Ig-CAD2 can, if desired, be substituted in whole or in part for the Ig-INSβ in the methods, kits, combinations, and compositions herein described.

In one embodiment of the present invention, the immunosuppressive factor for the down regulation of diabetogenic T cells comprises an immunoglobulin, or a portion thereof, linked to a protein fragment or peptide. In yet another embodiment, the immunoglobulin, or portion thereof, can bind, or is capable of binding, to an Fc receptor.

The present invention is also directed to methods, kits, combinations, and compositions comprising a pharmaceutically-effective amount of a composition comprising an immunoglobulin, or a portion thereof, linked to a peptide, wherein the immunoglobulin or portion thereof is aggregated.

The present invention is also directed to a methods, kits, combinations, and compositions, comprising: a pharmaceutically-effective amount of an immunoglobulin, or portion thereof, linked to a protein fragment or peptide, wherein the immunoglobulin, or portion thereof, can bind to an Fc receptor. Illustratively, the peptide comprises INSβ, GAD 1, or GAD2. In an additional embodiment, the composition comprises the property of being endocytosed by cells comprising the Fc receptor and processed by the cells to present the peptide to endogenous MHC Class II molecules, thereby substantially reducing or preventing activation of diabetogenic T cells specific for the peptide. In one embodiment, the peptide is inserted within a variable region of the immunoglobulin, or portion thereof.

The present invention is also directed to a use of a composition wherein the composition comprises a pharmaceutically-effective amount of an immunoglobulin, or portion thereof, linked to one or more peptides; wherein the immunoglobulin, or portion thereof, can bind to an Fc receptor and be endocytosed by an antigen presenting cell, and the one or more peptides, or fragments thereof, provide one or more T cell receptor engaging determinants for presentation on the surface of the antigen presenting cell upon endocytic processing for the preparation of a pharmaceutical composition for alleviating symptoms associated with type 1 diabetes for a subject in need.

The present invention also provides a method for presenting a T cell receptor engaging determinant on the surface of a professional or nonprofessional antigen presenting cell, comprising:

a) providing a composition comprising an immunoglobulin, or portion thereof, linked to one or more peptides derived from the group consisting of insulin and GAD; wherein the immunoglobulin, or portion thereof, can bind to an Fc receptor and be endocytosed by an antigen presenting cell; and the one or more peptides, or fragments thereof, provide one or more T cell receptor engaging determinants for presentation on the surface of the antigen presenting cell upon endocytic processing;

b) contacting the composition with at least one Fc receptor present on a surface of a professional or nonprofessional antigen presenting cell; wherein the composition is internalized by the antigen presenting cell; and c) endocytically processing the internalized composition to provide one or more T cell receptor engaging determinants; wherein the provided T cell receptor engaging determinants are presented on the surface of the antigen presenting cell.

In one embodiment, the T cell receptor engaging determinant is presented on the surface of the antigen presenting cells associated with at least on MHC complex.

Besides being useful for human treatment, the present invention is also useful for other subjects including veterinary animals, reptiles, birds, exotic animals and farm animals, including mammals, rodents, and the like. Mammals include horses, dogs, pigs, cats or primates, for example, a monkey, chimpanzee or a lemur. Rodents include rats, mice, squirrels, or guinea pigs.

In one embodiment of the present invention, methods, kits, combinations, and compositions containing at least one immunoglobulin, for example, INS, GAD, an insulin protein, a peptide derived from insulin, a diabetogenic epitope, or a T cell receptor engaging determinant, are provided to treat, prevent, suppress, or delay the onset of type 1 diabetes after expression of an IAA predisposition marker. In yet another embodiment, IL-10 is substantially not required for the treatment, prevention, suppression, or delay in the onset of type 1 diabetes.

In one embodiment, a method of treating, preventing, suppressing or delaying the onset of type 1 diabetes during the pre-insulitis stage of diabetes is provided. The method comprises administering to a subject a pharmaceutically-effective amount of a composition comprising an immunoglobulin, or a portion thereof, linked to a peptide, and where the immunoglobulin, or a portion thereof, is aggregated.

In yet another embodiment of the present invention, the aggregated immunoglobulin, or a portion thereof, can bind, or is capable of binding, to an Fc receptor and the peptide is presented to T cells in association with MHC class II molecules.

In one embodiment of the present invention, the subject is in preinsultis stage of type 1 diabetes. In yet another embodiment of the present invention, the subject has not yet undergone IAA seroconversion. In yet another embodiment of the present invention, the subject has seroconverted and produces autoantibodies against one or more β-cell associated antigens. In still another embodiment of the present invention, the subject is IAA-positive. And in yet another embodiment, the subject has not yet developed hyperglycemia.

The present invention is also directed to a method of treating, preventing, or delaying the onset of type 1 diabetes in a subject expressing a type 1 diabetes redisposition marker.

In another embodiment of the present invention, the aggregated immunoglobulin, or portion thereof, can bind, or is capable of binding, to an Fc receptor.

In yet another embodiment of the present invention, the peptide in which the immunoglobulin, or portion thereof, is presented to T cells in association with MHC class II molecules. In one embodiment, the peptide is an INSβ peptide.

In another embodiment of the present invention, the composition is endocytosed by cells having an Fc receptor and is processed and presented by the cells in association with MHC class II molecules thereby substantially reducing or preventing activation of diabetogenic T cells.

In yet another embodiment, the administration of the composition of the present invention to a subject predisposed for type 1 diabetes delays the onset of type 1 diabetes.

In another embodiment, the administration of the composition of the present invention to a subject induces production of IL-10.

In yet another embodiment of the present invention, the immunoglobulin comprises Ig-INSβ, Ig-GAD1, Ig-GAD2, or an immunoglobulin, or a portion thereof, linked to a peptide, for example a peptide derived from GAD65 or an insulin protein. In another embodiment of the present invention, the immunoglobulin, or a portion thereof, has more than one peptide linked to the immunoglobulin. In yet another embodiment, the immunoglobulin is soluble, for example, soluble Ig-INSβ. In still another embodiment of the present invention, the immunoglobulin, or a portion thereon, can be human or humanized, such as, for example, human IgG, such as IgG1, IgG2, IgG2a, IgG2b, IgG3, IgG4, IgGA, IgA1, IgA2, IgGE, IgD, IgE, or IgM. Illustratively, the Ig-INSβ can comprise agg Ig-INSβ, or soluble Ig-INSβ. In yet another embodiment of the present invention, the immunoglobulin is aggregated.

In yet another embodiment, the T cells are specific for the peptide. And in another embodiment, the peptide is a T cell receptor engaging determinant. In yet another embodiment, the peptide contains a diabetogenic epitope. In still another embodiment, the peptide is a INSβ peptide. In still another embodiment of the present invention, the peptide is derived from insulin. The another embodiment the peptide comprises a diabetogenic epitope.

In one embodiment of the present invention, the peptide is inserted within the variable region of the immunoglobulin, or a portion thereof, and the immunoglobulin, or a portion thereof, comprises human IgG or humanized IgG.

In still another embodiment of the present invention, the peptide is inserted within the variable region of the immunoglobulin, or a portion thereof, comprising the CDR1, CDR2, and/or CDR3 region. Illustratively, the peptide is inserted within the CDR3 region of the immunoglobulin, or a portion thereof, by deleting the D segment and insertion of the peptide.

In one embodiment, the peptide comprises GAD1 and/or GAD2.

In yet another embodiment of the present invention, the composition comprises IgINS (peptides derived from human insulin), IgGAD (peptides derived from GAD), IgINSβ, IgGAD1 and IgGAD2.

In yet another embodiment of the present invention, a method of treatment of type 1 diabetes in an at-risk subject expressing a predisposition marker with a composition comprising an immunoglobulin or portion thereof linked to a diabetogenic peptide wherein the composition is soluble. In one embodiment, the subject is in the pre-insulitis stage of type 1 diabetes, or expresses a predisposition marker IAA positive and/or GAD positive, or expresses a predisposition marker but has not yet progressed to a hyperglycemic stage.

In yet another embodiment, the composition comprises soluble Ig-INSβ.

In another embodiment of the present invention, the composition enhances IL-10 production in splenic T cells. In still another embodiment, the composition induces production of IL-10. In yet another embodiment of the present invention, the composition induces production of IL-10 by APCs thereby enhancing peripheral tolerance to the onset of diabetes at the pre-insulitic stage. In another embodiment the composition of the present invention induces production of TGFβ and/or IL-10 producing cells. In yet another embodiment, the composition when administered to a subject delays the onset of type 1 diabetes. In still another embodiment, the subject is at the pre-insulitis stage and/or following seroconversion.

In one embodiment of the present invention, the T cells are nonproliferative antigen specific T cells.

In yet another embodiment of the present invention, the receptor is an Fcγ receptor. In another embodiment of the present invention, the aggregated Ig-INSβ compositions cross-link Fcγ receptors.

In one embodiment of the present invention, the composition is administered daily, weekly, or monthly. Illustratively, the composition is administered weekly, and achieve, for example, full suppression of type 1 diabetes.

In another embodiment of the present invention, the MHC complex comprises the MHC Class II molecule.

In one embodiment of the present invention, the composition comprises Ig-INSβ, Ig-GAD1, IgGAD2 or an immunoglobulin or a portion thereof linked to a peptide derived from GAD65.

In one embodiment of the present invention, the composition is endocytosed by cells having an Fc receptor and is processed and presented by the cells in association with MHC class II molecules thereby substantially reducing or preventing activation of diabetogenic T cells.

In another embodiment of the present invention, the T cells are antigen specific.

In one embodiment of the present invention, a composition is provided comprising an immunoglobulin or portion thereof linked to a protein fragment or peptide wherein the immunoglobulin or portion thereof is capable of binding to an Fc receptor, the peptide being selected from the group consisting of peptides derived from INS and GAD and more specifically INSβ, GAD 1 and GAD2, the composition having the property of being endocytosed by cells bearing the Fc receptor and processed and presented by the cells to present the peptide to endogenous MHC Class II molecules, thereby substantially reducing or preventing activation of diabetogenic T cells specific for the peptide.

In another embodiment of the present invention, the composition is selected from the group consisting of agg Ig-INSβ and soluble Ig-INSβ.

In one embodiment of the present invention, the peptide is a T cell receptor engaging determinant.

In another embodiment of the present invention, the peptide is inserted within the variable region of the immunoglobulin or portion thereof.

In one embodiment of the present invention, the peptide is inserted within the region selected from the group consisting of CDR1, CDR2 and CDR3.

In another embodiment of the present invention, the immunoglobulin or portion thereof is human IgG or derived from human IgG or humanized IgG.

In one embodiment of the present invention, the immunoglobulin or portion thereof is in an aggregated form.

In another embodiment of the present invention, the composition is in soluble form.

In one embodiment of the present invention, the composition further comprises a pharmaceutically acceptable carrier.

In another embodiment of the present invention, a use of a composition is provided wherein the composition comprises an immunoglobulin or portion thereof linked to one or more peptides wherein the immunoglobulin or portion thereof is capable of binding to an Fc receptor and being endocytosed by an antigen presenting cell and the one or more peptides or fragments thereof provides a T cell receptor antagonist for presentation on the surface of the antigen presenting cell upon endocytic processing for the preparation of a pharmaceutical composition for alleviating symptoms associates with type 1 diabetes for a patient in need.

In another embodiment of the present invention, the immunoglobulin or portion thereof is comprised of at least part of a domain of a constant region of an immunoglobulin.

In one embodiment of the present invention, the provided T cell receptor engaging determinant or epitope is presented on the surface of the antigen presenting cells associated with at least one MHC complex.

Figure 9:
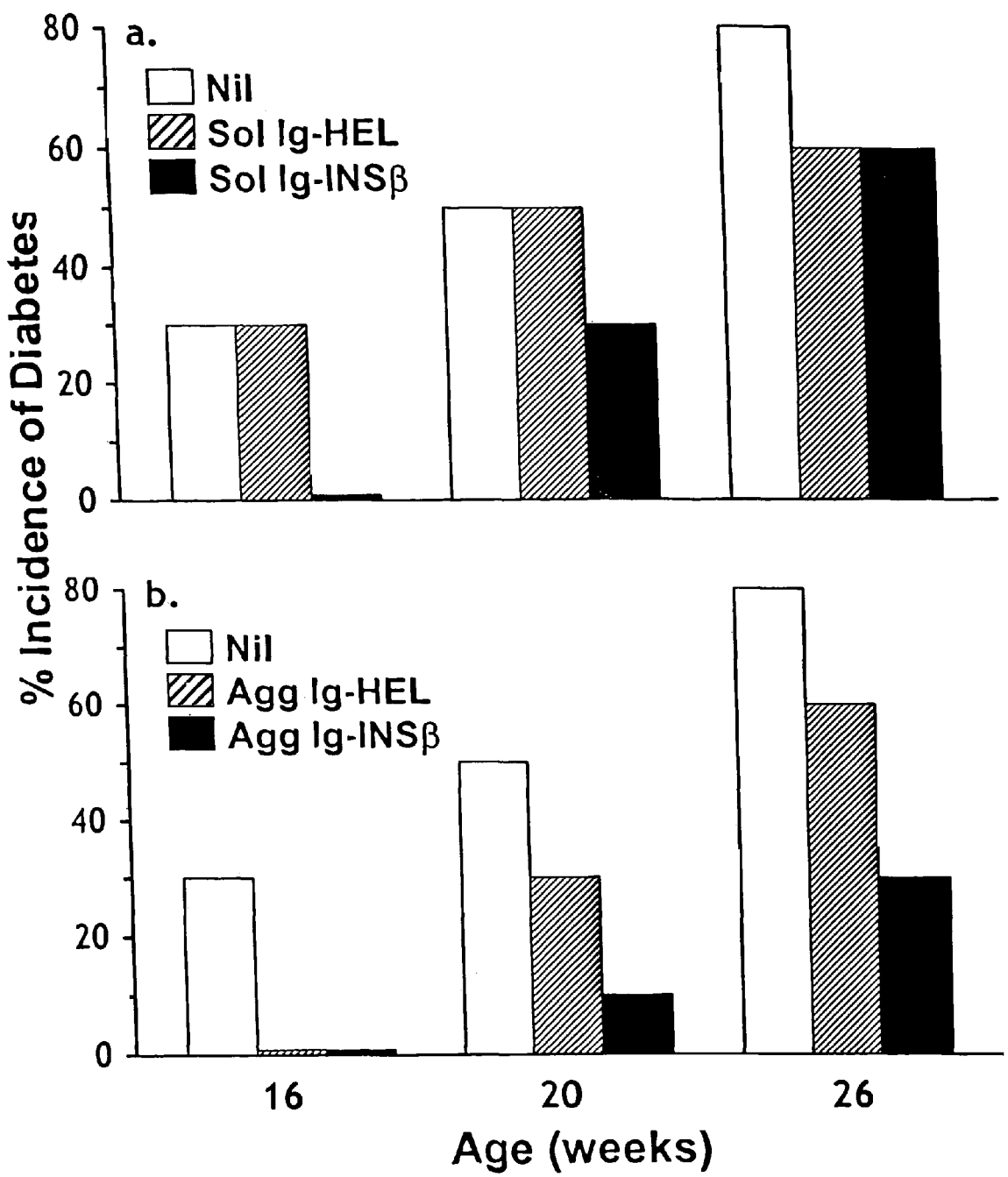
FIG. 9 shows that treatment with agg Ig-INSβ at the pre-insulitis stage leads to effective suppression of diabetes.
Figure 10:
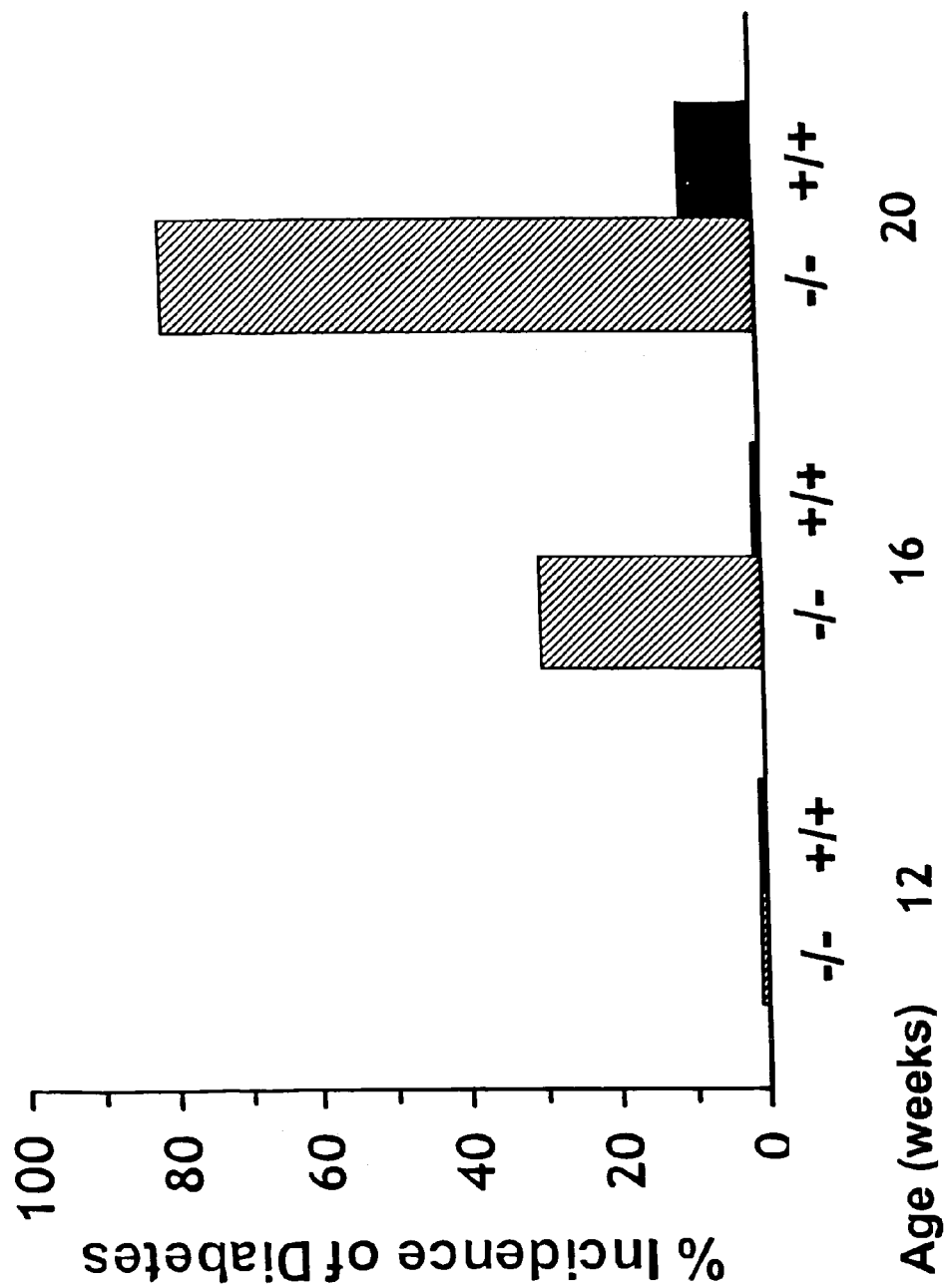
FIG. 10 shows that administration of agg Ig-INSβ into IL-10$^{-/-}$ NOD mice at the pre-insulitis stage does not delay onset of diabetes; and, FIG. 11 illustrates that splenic and islet-infiltrating INSβ-specific T cells mount differential IFNγ responses upon stimulation with agg Ig-INSβ.

IL-10's function in diabetes is dependent on a number of factors (24-29). Systemic IL-10 has been shown to prevent diabetes in NOD mice while local production of IL-10 accelerated the development of disease in the NOD strain (24-26). As shown in the following Examples, agg Ig-INSβ was injected intraperitoneally and IL-10 was produced by APCs or "regulatory" T cells in a systemic manner; yet, diabetes was not delayed even though a peripheral tolerance mechanism by lack of costimulation was in place. In contrast, when agg Ig-INSβ was administered intraperitoneally at the pre-insulitis stage it was much more effective than the soluble form for suppression of diabetes (FIG. 9). The involvement of IL-10 in this pre-insulitis regimen is crucial as IL-10-deficient mice treated with agg Ig-INSβ displayed no delay of diabetes (FIG. 10). Thus, IL-10 appears to display a stimulatory function when its production is triggered after IAA-seroconversion but supports a modulatory function when produced at the pre-insulitis stage. One explanation for this observation is that states that encounter IL-10 by diabetogenic T cells within the islets promote stimulation while exposure of the diabetogenic T lymphocytes prior to migration to the islets sustains modulation. Indeed, soluble Ig-INSβ given to mice after IAA-seroconversion supported delay and partial protection against diabetes indicating that diabetogenic T cells remain susceptible to tolerance while agg Ig-INSβ, which would also support peptide presentation with minimal or no costimulation but includes IL-10 production by APCs, had no protective effect.

Figure 11:
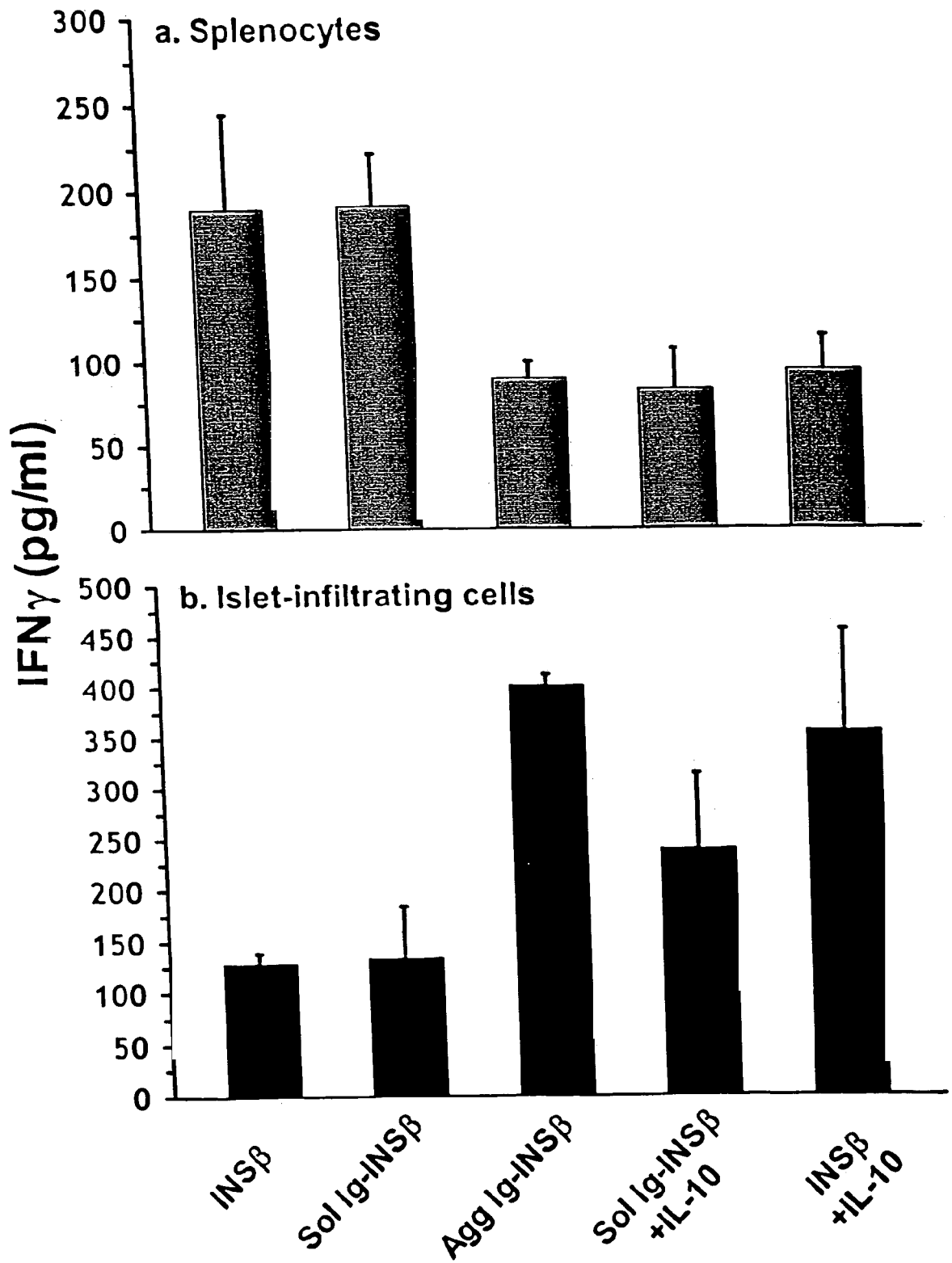

At the age of 10 to 12 weeks, a time when the mice have seroconverted to become IAA-positive, insulitis is usually in place and diabetogenic T cells have already infiltrated the islets (4). However, these T cells, although vulnerable to treatment with soluble Ig-INSβ, seem to resist the aggregated form of the chimera. Since both aggregated and soluble forms of Igs do not up-regulate costimulatory molecules (20) but only the aggregated form induces IL-10 production by APCs, it is likely that diabetogenic T cells exposed to IL-10 within the islets resist tolerance. Indeed these cells were stimulated to produce IFNγ upon incubation with agg Ig-INSβ or even INSβ peptide and rIL-10 (FIG. 11).

It has been previously shown that local IL-10 produced within the islets up-regulate ICAM-1 on pancreatic vascular endothelium and facilitate acceleration of insulitis (24). At the pre-insulitis stage, the diabetogenic T cells may be exposed to IL-10 outside of the islets, most likely resulting in synergy with lack of costimulation leading to effective delay of diabetes. In fact, splenic T cells from 14 week old mice down-regulated IFNγ production when incubated with agg Ig-INSβ or INSβ and rIL-10 (FIG. 11). The notion that encounter of T cells with IL-10 prior to migration to the islets has a different outcome from encounters that happen within the islets is supported by studies demonstrating that delivery of IL-10 at a young age and before insulitis takes place delays diabetes (27, 48) while prevention of IL-10-IL-10R interactions before insulitis exacerbates the disease (28). Also, the observation bodes well with the modulatory function of transgenic and viral vector delivered IL-10, which would modulate T cells prior to migration to the islets (29, 49, 50). However, it remains unclear how injection of anti-IL-10 antibody at the pre-insulitis stage delays diabetes (27, 49) despite that agg Ig-INSβ treatment was unable to delay the disease in IL-10-deficient mice (see FIG. 10). Also, injection of anti-IL-10 antibody during treatment with agg at the pre-insulitis stage delayed the disease (not shown) and this function may be related to a cross-reactivity with other cytokines or molecules involved in regulation of the pathogenesis of diabetes (49). Since agg Ig-INSβ induced T cells producing TGFβ in addition to IL-10 (FIG. 6), it remains unclear how such a suppressive cytokine could not lead to a delay of diabetes.

Overall, the Ig delivery system of the present invention provides an approach that displays under different circumstances distinct modulatory functions and can be adapted to delay diabetes in a human or non-human patient before the development of insulitis or in predisposed individuals who have seroconverted and produce autoantibodies against one or more β-cell associated antigens, such as, for example, IAA-positive individuals, and can also lead to suppression of type 1 diabetes.

While not intending to be bound by theory, research suggests that IL-10 can act as an immunosuppressive. It has now been discovered, however, that this function can be exploited against autoimmunity in the treatment of type 1 diabetes. Variable effects have been observed when IL-10 was utilized for suppression of type 1 diabetes. Herein, insulin 13 chain ("INSβ") 9-23 peptide is genetically expressed on an immunoglobulin (Ig) chimera and the resulting Ig-INSβ facilitated control of endogenous IL-10 and analysis of its function against diabetes. Soluble ("sol") Ig-INSβ supported efficient peptide presentation while aggregated ("agg") Ig-INSβ cross-linked Fcγ receptors additionally triggering IL-10 production by the antigen presenting cells. Both forms were then tested for suppression of diabetes in NOD mice at the pre-insulitis stage and following seroconversion to insulin autoantibody ("IAA") production. Soluble Ig-INSβ displayed dose dependent delay of diabetes when given at either stage. However, aggregated Ig-INSβ, which induced IL-10- and TGFβ-producing T cells, thus involving sustained endogenous IL-10, was protective against diabetes when given before development of insulitis but had no effect in predisposed mice positive for IAA. This discrepancy correlated with variable susceptibility to IL-10 among islet and peripheral pathogenic T cells. Thus, IL-10 synergizes with peripheral tolerance at the pre-insulitis stage while in IAA-positive mice, where islet infiltration is progressive, disease suppression is more effective in the absence of IL-10. Thus, it is contemplated herein that expression of diabetogenic peptide on Ig displays broad efficacy against the diverse T cell specificities responsible for diabetes in NOD mice.

To test this premise, the I-A$^{g7}$-restricted insulin beta chain (INSβ) 9-23 peptide (30, 31) was genetically engineered into the variable region of an IgG2b molecule and the soluble and aggregated forms of the resulting Ig-INSβ chimera were tested for presentation to diabetogenic T cells and suppression of diabetes before and after seroconversion into production of insulin-specific autoantibodies (IAA). The results indicate that soluble Ig-INSβ displays partial protection against diabetes both at the pre-insulitis stage and in IAA-positive animals while agg Ig-INSβ, which induced IL-10- and TGFβ-producing cells, is effective prior to but not after IAA-seroconversion. The asymmetrical function of endogenous IL-10 may be related to variable susceptibility of the diabetogenic T cells to the cytokine depending on whether exposure occurs before or after migration to the islets.

Figure 4:
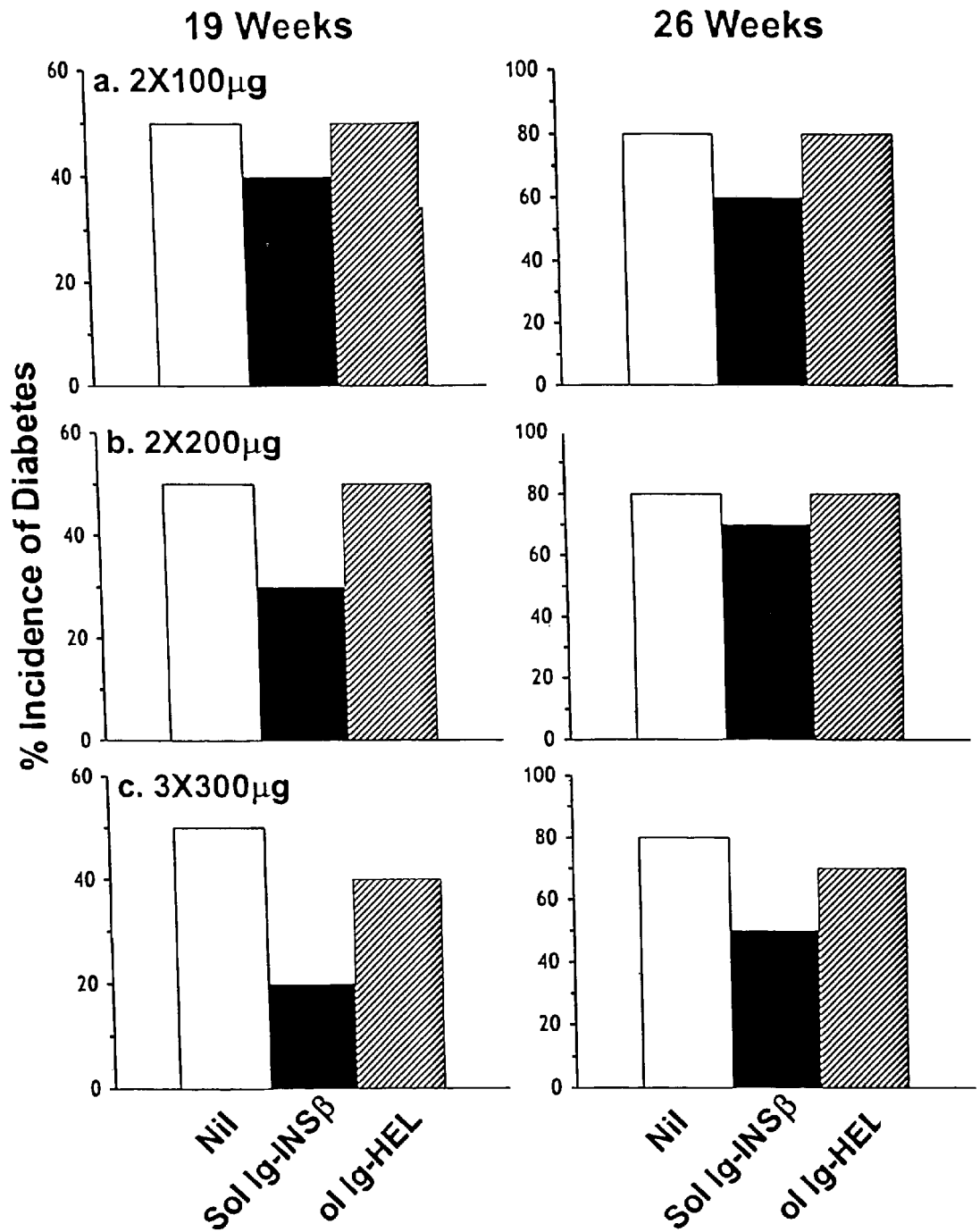
FIG. 4 shows dose dependent suppression of diabetes by soluble Ig-INSβ in IAA-positive NOD mice.
Figure 5:
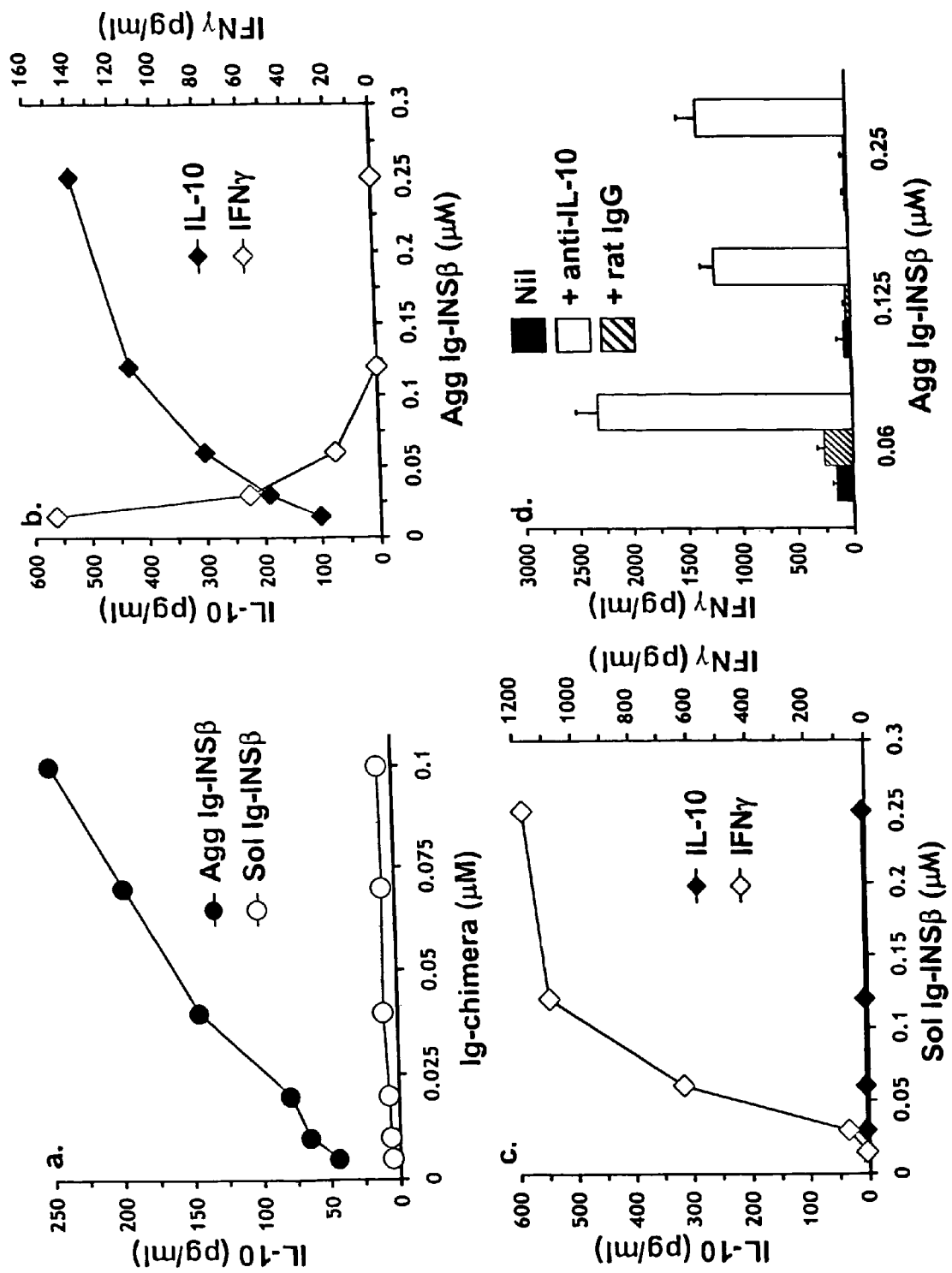
FIG. 5 shows that IL-10 secreted by APCs during presentation of agg Ig-INSβ antagonizes the production of IFNγ by INSβ-specific T cells.
Figure 6:
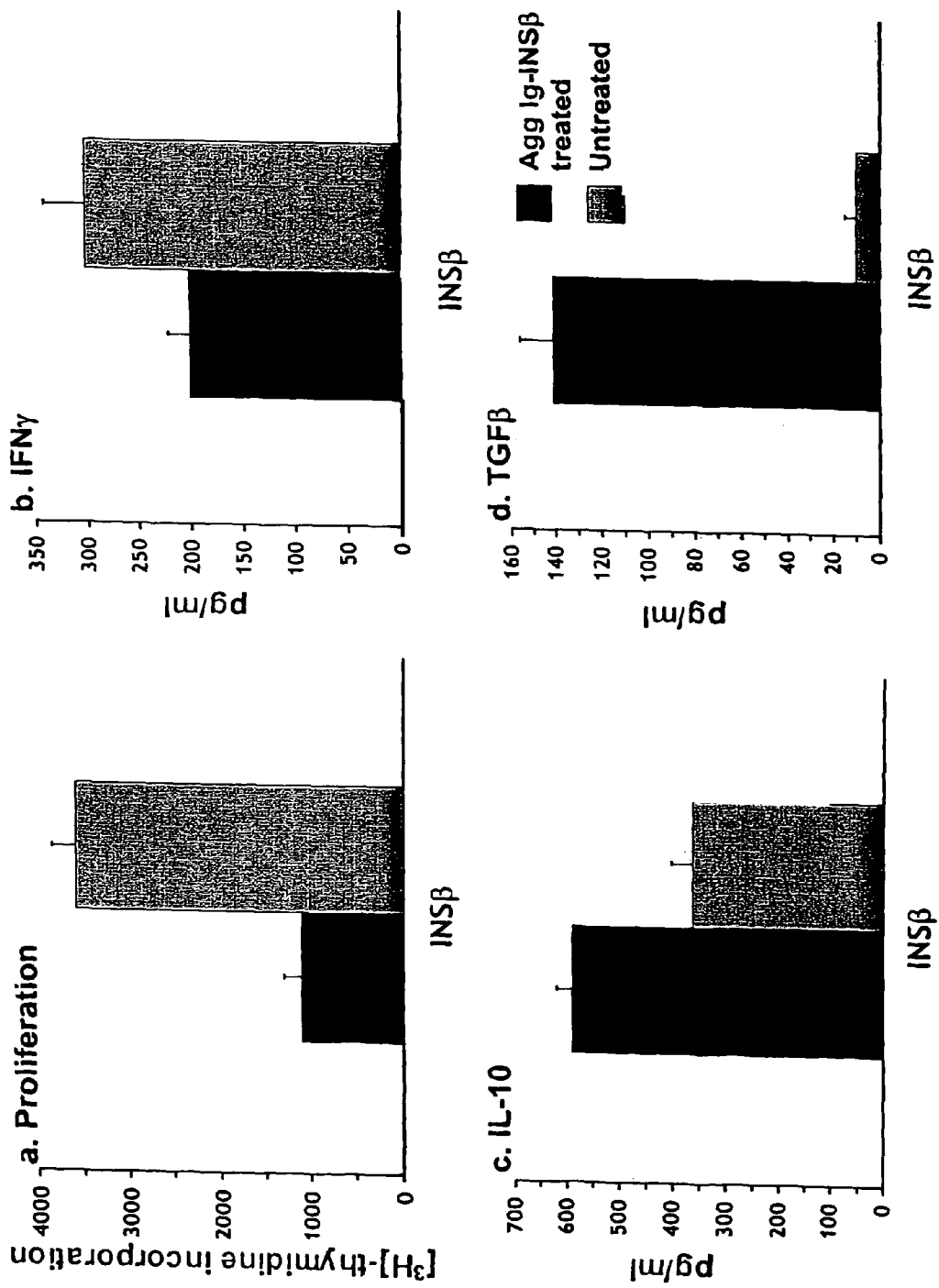
FIG. 6 shows that agg Ig-INSβ reduces Th1 responses but supports production of IL-10 and TGFβ upon administration into NOD mice.
Figure 7:
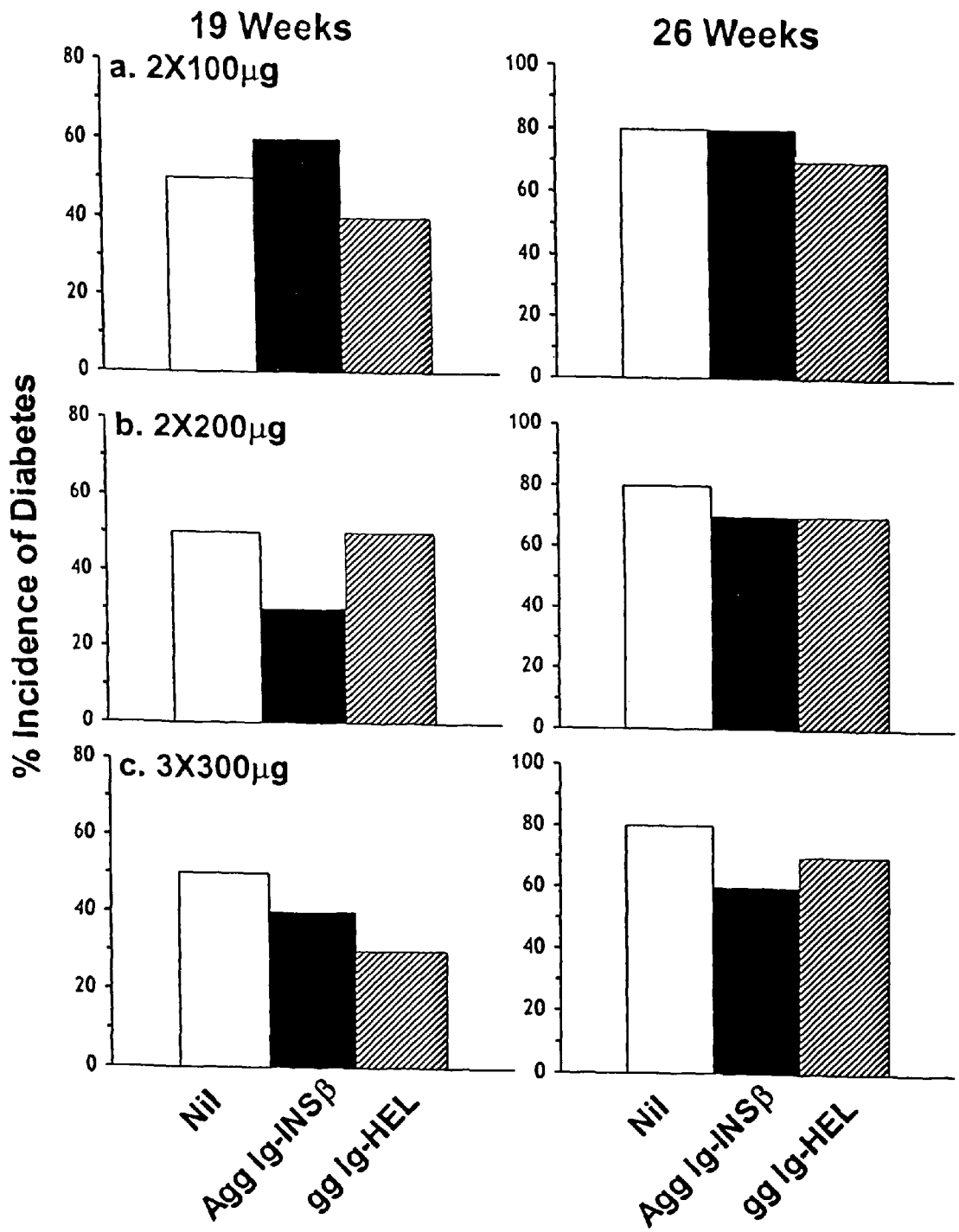
FIG. 7 shows that agg Ig-INSβ displays no significant delay of diabetes in IAA-positive mice.

The present invention demonstrates that soluble Ig-INSβ, which does not induce IL-10 production upon binding to FcγRs, displays down-regulatory functions in vivo and delays the onset of diabetes in IAA-seropositive NOD mice (FIGS. 4, 5 and 7). Although complete suppression has not been achieved, the observed delay remains of great significance as the approach provides a means to treat predisposed subjects before the disease progresses to an irreversible stage. Also, continuous weekly administration of soluble Ig-INSβ can fully protect against the disease in IAA-positive mice. Because Ig-INSβ uses the same IgG2b isotype as Ig-PLP1 and Ig-MOG (22, 23) and like these chimeras may not induce the up-regulation of costimulatory molecules on APCs upon injection into animals free of adjuvant (20), the resulting INSβ presentation in vivo most likely lacks costimulatory leading to a peripheral tolerance-like mechanism effective against diabetogenic T cells. On the other hand, it is shown that agg Ig-INSβ, which cross-links FcγR, induces IL-10 production by APCs (FIG. 5). As a consequence, such IL-10 secretion by APCs led to down-regulation of IFNγ production by specific T cells that were engaged to the APCs through INSβ peptide derived from agg (FIG. 5). Moreover, agg Ig-INSβ stimulated the induction of IL-10- and TGFβ-producing T cells in vivo (FIG. 6). Yet, agg Ig-INSβ was unable to suppress diabetes or even sustain partial modulatory functions that usually arise as a consequence of peptide presentation with minimal or no costimulation in those IAA-positive mice (FIG. 7). Thus, mobilization of endogenous IL-10, whether by stimulation of APCs or induction of "regulatory" T cells in animals that have seroconverted to IAA production and initiated insulitis, seems to antagonize peripheral tolerance and support disease progression.

In one embodiment of the present invention, the compounds are formulated as an injectable formulation and comprise, for example, an aqueous solution or suspension of the compounds suitable for intravenous delivery. When preparing the composition for injection, particularly for intravenous delivery, illustratively, the continuous phase comprises an aqueous solution of tonicity modifiers, buffered to a pH below 7, for example, or below 6, for example. The tonicity modifiers comprise, for example, sodium chloride, glucose, mannitol, trehalose, glycerol, or other pharmaceutical agents that renders the osmotic pressure of the formulation isotonic with blood. Alternatively, when a larger quantity of the tonicity modifier is used in the formulation, it can be diluted prior to injection with a pharmaceutically acceptable diluent to render the mixture isotonic with blood.

In another embodiment of the present invention, a preservative is added to the formulation. Illustratively, a preservative includes benzalkonium chloride, propylparabem, butylparaben, chlorobutanol, benzyl alcohol, phenol, sodium benzoate, or EDTA.

The compositions of the present invention can further comprise a pharmaceutically acceptable carrier. The carrier materials that can be employed in making the compositions of the present invention are any of those commonly used excipients in pharmaceutics and should be selected on the basis of compatibility with the pharmaceutical agent and the release profile properties of the desired dosage form. Illustratively, a pharmaceutical excipient except active drugs are chosen below as examples:

(a) Binders such as acacia, alginic acid and salts thereof, cellulose derivatives, methylcellulose, hydroxyethyl cellulose, hydroxypropyl cellulose, magnesium aluminum silicate, polyethylene glycol, gums, polysaccharide acids, bentonites, hydroxypropyl methylcellulose, gelatin, polyvinylpyrrolidone, polyvinylpyrrolidone/vinyl acetate copolymer, crospovidone, povidone, polymethacrylates, hydroxypropylmethylcellulose, hydroxypropylcellulose, starch, pregelatinized starch, ethylcellulose, tragacanth, dextrin, microcrystalline cellulose, sucrose, or glucose, and the like.

(b) Disintegration agents such as starches, pregelatinized corn starch, pregelatinized starch, celluloses, cross-linked carboxymethylcellulose, sodium starch glycolate, crospovidone, cross-linked polyvinylpyrrolidone, croscarmellose sodium, a calcium, a sodium alginate complex, clays, alginates, gums, or sodium starch glycolate, and any disintegration agents used in tablet preparations.

(c) Filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

(d) Surfactants such as sodium lauryl sulfate, sorbitan monooleate, polyoxyethylene sorbitan monooleate, polysorbates, polaxomers, bile salts, glyceryl monostearate, Pluronic™ line (BASF), and the like.

(e) Solubilizer such as citric acid, succinic acid, fumaric acid, malic acid, tartaric acid, maleic acid, glutaric acid sodium bicarbonate and sodium carbonate and the like.

(f) Stabilizers such as any antioxidation agents, buffers, or acids, and the like, can also be utilized.

(g) Lubricants such as magnesium stearate, calcium hydroxide, talc, sodium stearyl fumarate, hydrogenated vegetable oil, stearic acid, glyceryl behapate, magnesium, calcium and sodium stearates, stearic acid, talc, waxes, Stearowet, boric acid, sodium benzoate, sodium acetate, sodium chloride, DL-leucine, polyethylene glycols, sodium oleate, or sodium lauryl sulfate, and the like.

(h) Wetting agents such as oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, or sodium lauryl sulfate, and the like.

(i) Diluents such lactose, starch, mannitol, sorbitol, dextrose, microcrystalline cellulose, dibasic calcium phosphate, sucrose-based diluents, confectioner's sugar, monobasic calcium sulfate monohydrate, calcium sulfate dihydrate, calcium lactate trihydrate, dextrates, inositol, hydrolyzed cereal solids, amylose, powdered cellulose, calcium carbonate, glycine, or bentonite, and the like.

(j) Anti-adherents or glidants such as talc, corn starch, DL-leucine, sodium lauryl sulfate, and magnesium, calcium, or sodium stearates, and the like.

(k) Pharmaceutically compatible carrier comprises acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, or pregelatinized starch, and the like.

Additionally, drug formulations are discussed in, for example, Hoover, John E., *Remington's Pharmaceutical Sciences*, Mack Publishing Co., Easton, Pa. 1975. Another discussion of drug formulations can be found in Liberman, H. A. and Lachman, L., Eds., *Pharmaceutical Dosage Forms*, Marcel Decker, New York, N.Y., 1980.

In making the compositions of the present invention, the components can be mixed with a pharmaceutically acceptable excipient, diluted by the excipient or enclosed within such a carrier, which can be in the form of a capsule, sachet, paper or other container. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents, such as talc, magnesium stearate and mineral oil; wetting agents; emulsifying and suspending agents; preserving agents, such as methyl- and propylhydroxybenzoates; sweetening agents; and flavoring agents.

When the excipient serves as a diluent, it can be a solid, semi-solid or liquid material, which acts as a vehicle, carrier or medium for the active ingredient. Thus, the compositions can be in the form of a tablet, pill, powder, lozenge, sachet, cachet, elixir, troche, suspension, emulsion, solution, syrup, aerosol (as a solid or in a liquid medium), soft and hard gelatin capsule, sterile packaged powder, dispensable powder, granule, or liquid.

Tablet forms can include, for example, one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents and pharmaceutically compatible carriers. In one embodiment of the present invention, the manufacturing processes may employ one or a combination of methods: (1) dry mixing, (2) direct compression, (3) milling, (4) dry or non-aqueous granulation, (5) wet granulation, or (6) fusion. Lachman et al., *The Theory and Practice of Industrial Pharmacy* (1986). Such tablets may also comprise film coatings, which disintegrate upon oral ingestion or upon contact with diluent.

In another embodiment of the present invention, solid compositions, such as tablets, are prepared by mixing therapeutic agent of the present invention with a pharmaceutical excipient to form a solid preformulation composition containing a homogeneous mixture of the therapeutic agent and excipient. When referring to these preformulation compounds as homogeneous, it is meant that the agents are evenly throughout the composition so that the composition may be readily subdivided into equally effective unit dosage forms, such as tablets, pills and capsules. This solid preformulation is then subdivided into unit dosage forms of the type described herein.

Compressed tablets are solid dosage forms prepared by compacting a formulation containing a therapeutic agent and excipient selected to aid the processing and improve the properties of the product. The term "compressed tablet" generally refers to a plain, uncoated tablet for oral ingestion, prepared by a single compression or by pre-compaction tapping followed by a final compression.

The tablets or pills of the present invention may be coated or otherwise compounded to provide a dosage form affording the advantage of improved handling or storage characteristics. For example, the tablet or pill can comprise an inner dosage and an outer dosage component, the latter being in the form of an envelope over the former. In another embodiment, the compositions of the present invention are administered by intravenous (IV) infusion or intra-arterial administration over a desired period (for example, bolus injection, 5 min, 15 min, 30 min, 1 hr, 2 hr, 3 hr, 6 hr, 24 hr, 48 hr, 72 hr or 96 hour infusions). In one embodiment of the present invention the period of administration is no greater than about 3 hours.

The present invention is also directed to a therapeutic method of treating a condition or disorder where treatment with an anti-diabetic type-1 agent is indicated. The method comprises the administration of one or more of the pharmaceutical compositions of the present invention to a subject in need thereof. In one embodiment, the dosage regimen to prevent, give relief from, or ameliorate the condition or disorder corresponds to once-a-day or twice-a-day dosages, and can include, for example, a 0.0001 mg/kg, 0.0005 mg/kg, 0.001 mg/kg, 0.01 mg/kg, 0.05 mg/kg, 0.1 mg/kg, 0.5 mg/kg, 1 mg/kg, 2 mg/kg, 5 mg/kg, 10 mg/kg, 15 mg/kg, 20 mg/kg, 30 mg/kg, 40 mg/kg, 50 mg/kg, 60 mg/kg, 70 mg/kg, 80, mg/kg, 90 mg/kg, 100 mg/kg, 110 mg/kg, 120 mg/kg, 130 mg/kg, 140 mg/kg, 150 mg/kg, 160 mg/kg, 170 mg/kg, 180 mg/kg, 190 mg/kg, 200 mg/kg, 220 mg/kg, 240 mg/kg, 250 mg/kg, 500 mg/kg, 750 mg/kg, or 1,000 mg/kg (by body weight of the subject) of a therapeutic agent of the present invention, and can be modified in accordance with a variety of factors. These specific mg/kg amounts can vary, for example, from about 0:01% to about 20% or more, depending on the application and desired therapeutic result. Other factors include the type of subject, the age, weight, sex, diet, and medical condition of the subject and the severity of the disease. Thus, the dosage regimen actually employed can vary widely and therefore deviate from the dosage regimen set forth above. Unit dosage forms of the compositions of the present invention can typically contain, for example, about 1 ng to about 2000 mg, about 0.001 mg to about 750 mg, about 0.01 mg to about 500 mg, about 0.1 mg to about 300 mg or about 1 mg to about 100 mg. Illustratively, such unit dosage forms can contain about 0.001 mg, or about 0.01 mg, or about 0.1 mg, or about 1 mg, or about 2 mg, or about 5 mg, or about 10 mg, or about 15 mg, or about 20 mg, or about 30 mg, or about 40 mg, or about 50 mg, or about 60 mg, or about 70 mg, or about 80, mg, or about 90 mg, or about 100 mg, or about 110 mg, or about 120 mg, or about 130 mg, or about 140 mg, or about 150 mg, or about 160 mg, or about 170 mg, or about 180 mg, or about 190 mg, or about 200 mg, or about 300 mg, or about 400 mg, or about 500 mg, or about 750 mg, or about 1,000 mg of a therapeutic agent of the present invention. Illustratively, unit dosage forms each contain about 0.1 mg, 1 mg, 5 mg 10 mg, 15 mg, 20 mg, 40 mg, 80 mg, 100 mg, 250 mg, 500 mg, or 1000 mg of a therapeutic agent of the present invention. The dosage unit form can be selected to accommodate the desired frequency of administration used to achieve the specified daily dosage. Preferably, a composition of the invention will be administered to a subject in an amount sufficient to about 0.1 to about 15 mg, more preferably about 0.5 to about 10 mg, and even more preferably about 1 to about 5 mg of the active agent, for example soluble INSβ.

The amount of the unit dosage form of the pharmaceutical composition that is administered and the dosage regimen for treating the condition or disorder depends on a variety of factors, including the age, weight, sex and medical condition of the subject, the severity of the condition or disorder, the route and frequency of administration, and thus can vary widely, as is well known. Illustratively, where the subject is a child or a small animal (for example, a dog), a relatively low amount of the agent in the dose range of about 0.1 mg to about 20 mg is likely to provide blood serum concentrations consistent with therapeutic effectiveness. Where the subject is an adult human or a large animal (for example, a horse), achievement of such blood serum concentrations of the agent are likely to require dose units containing a relatively greater amount of the agent, for example, a 15 mg, 20 mg, 30 mg, 40 mg, 80 mg, or 100 mg dose for an adult human, or a 100 mg, 250 mg, 500 mg, or 1000 mg dose for an adult horse. These specific amounts can vary, for example, from between about 0.01% to about 20% or more, depending on the application and desired therapeutic result.

The amount of therapeutic agent necessary to elicit a therapeutic effect can be experimentally determined based on, for example, the absorption rate of the agent into the blood serum, the bioavailability of the agent, and the amount of protein binding of the agent. It is understood, however, that specific dose levels of the therapeutic agents of the present invention for any particular subject depends upon a variety of factors including the activity of the specific compound employed, the age, body weight, general health, sex, and diet of the subject (including, for example, whether the subject is in a fasting or fed state), the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for subject administration. Studies in animal models generally may be used for guidance regarding effective dosages for treatment of diabetic disorders or diseases in accordance with the present invention. In terms of treatment protocols, it should be appreciated that the dosage to be administered will depend on several factors, including the particular agent that is administered, the route administered, the condition of the particular subject, etc. Generally speaking, one will desire to administer an amount of the compound that is effective to achieve a serum level commensurate with the concentrations found to be effective in vitro for a period of time effective to elicit a therapeutic effect. Thus, where a compound is found to demonstrate in vitro activity at, for example, 10 ng/ml, one will desire to administer an amount of the drug that is effective to provide at least about a 10 ng/ml concentration in vivo for a period of time that elicits a desired therapeutic effect, for example, lowering blood glucose level to acceptable levels, or improvement or elimination of symptoms, and other indicators as are selected as appropriate measures by those skilled in the art. Determination of these parameters is well within the skill of the art. These considerations are well known in the art and are described in standard textbooks.

Initial treatment of a subject suffering from a condition or disorder where treatment with an anti-diabetic type 1 agent is indicated can begin with the dosages indicated above. Treatment is generally continued as necessary over a period of hours, days, weeks to several months or years until the condition or disorder has been controlled or eliminated. In one embodiment, a composition of the invention can be administered to a subject in a plurality of dosages. Illustratively, such administration can comprise a continuos (for example, by administration by an osmotic pump, patch, gel, cream, or infusion device), hourly, daily, weekly, bi-weekly, or monthly administration of the composition for any desired duration, for example for a period of about 1 week, about 2 weeks, about 1 month or more, about 3 months or more, about 6 months or more, about 9 months or more, about 1 year or more, about 3 years or more, about 5 years or more, or throughout the subject's life.

Subjects undergoing treatment with the compositions disclosed herein can be routinely monitored by any of the methods well known in the art to determine the effectiveness of therapy. Continuous analysis of such data permits modification of the treatment regimen during therapy so that optimal effective amounts of compounds of the present invention are administered at any point in time, and so that the duration of treatment can be determined as well. In this way, the treatment regimen/dosing schedule can be rationally modified over the course of therapy so that the lowest amount of an anti-diabetic type 1 agent exhibiting satisfactory effectiveness is administered, and so that administration is continued only so long as is necessary to successfully treat the condition or disorder.

The present methods, kits, and compositions can also be used in combination ("combination therapy") with another pharmaceutical agent that is indicated for treating, preventing, suppressing or delaying the onset of type 1 diabetes, such as, for example, insulin, an alpha-glucosidase inhibitor, an insulin sensitizer, or a hyperglycemic agent, which are commonly administered to treat the symptoms and/or complications related to this disorder. These drugs have certain disadvantages associated with their use. Some of these drugs are not completely effective in the treatment of the aforementioned conditions and/or produce adverse side effects, such as hypoglycemia, microvascular disease, and macrovascular disease. However, when used in conjunction with the present invention, that is, in combination therapy, many if not all of these unwanted side effects can be reduced or eliminated. The reduced side effect profile of these drugs is generally attributed to, for example, the reduce dosage necessary to achieve a therapeutic effect with the administered combination.

The phrase "combination therapy" embraces the administration of a composition of the present invention in conjunction with another pharmaceutical agent that is indicated for treating or preventing type 1 diabetes in a subject, as part of a specific treatment regimen intended to provide a beneficial effect from the co-action of these therapeutic agents for the treatment of type 1 diabetes. The beneficial effect of the combination includes, but is not limited to, pharmacokinetic or pharmacodynamic co-action resulting from the combination of therapeutic agents. Administration of these therapeutic agents in combination typically is carried out over a defined time period (usually substantially simultaneously, minutes, hours, days, weeks, months or years depending upon the combination selected). "Combination therapy" generally is not intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, where each therapeutic agent is administered at a different time, as well as administration of these therapeutic agents, or at least two of the therapeutic agents, in a substantially simultaneous manner. Substantially simultaneous administration can be accomplished, for example, by administering to the subject a single injection, tablet or capsule having a fixed ratio of each therapeutic agent or in multiple, single injections, capsules, or tablets for each of the therapeutic agents. Sequential or substantially simultaneous administration of each therapeutic agent can be effected by any appropriate route. For example, the composition of the present invention can be administered orally, percutaneously, intravenously, intramuscularly, and/or directly absorbed through mucosal membranes, for example, while the other therapeutic agent of the combination can be administered by any appropriate route for that particular agent, including, but not limited to, an oral route, a percutaneous route, an intravenous route, an intramuscular route, or by direct absorption through mucous membrane tissues. The sequence in which the therapeutic agents are administered is not narrowly critical. "Combination therapy" also can embrace the administration of the therapeutic agents as described above in further combination with other biologically active ingredients, such as, but not limited to, (1) anti-inflammatory agents, such as a steroidal or nonsteroidal anti-inflammatory drug, and/or a 5-lipoxygenase inhibitor; or (2) an agent for treating cardiovascular disease or disorders, such as, for example, an antihypertensive agent, including, for example, an angiotensin converting enzyme inhibitor (ACE-inhibitor), an alpha-adrenergic agonist, a beta-adrenergic agonist, an alpha-adrenergic blocker, an angiotensin II receptor antagonist; a diuretic, including, for example, an aldosterone antagonist, a benzothiadiazine derivative, an organomercurial, a purine, a steroid (for example, canrenone, oleandrin, spironolactone), a sulfonamide derivative, or a uracil; an antianginal agent; an antiarrhythmic agent; an antiarteriosclerotic agent; an antihyperlipoproteinemic agent; an anicholelithogenic agent; an anticholesteremic agent; an antihypercholesterolemic agent; an antihyperlipidemic agent; an antihypertensive agent; an antihypotensive agent; an antilipidemic agent; a calcium channel blocker; a cardiac depressant agent; a dopamine receptor agonist; a dopamine receptor antagonist; a HMG CoA reductase inhibitor; an hypocholesteremic agent; a hypolipidemic agent; a hypotensive agent; a monoamine oxidase inhibitor; a muscle relaxant; a potassium channel activator; a pressor agent; a serotonin uptake antagonist; a thrombolytic agent; a vasodilator agent; a vasopressor agent; or a vasoprotectant agent (Based in part upon the list provided in *The Merck Index*, Merck & Co. Rahway, N.J. (2001), which is hereby incorporated by reference); and with non-drug therapies, such as, but not limited to, surgery.

The therapeutic compounds which make up the combination therapy may be a combined dosage form or in separate dosage forms intended for substantially simultaneous administration. The therapeutic compounds that make up the combination therapy may also be administered sequentially, with either therapeutic compound being administered by a regimen calling for two step administration. Thus, a regimen may call for sequential administration of the therapeutic compounds with spaced-apart administration of the separate, active agents. The time period between the multiple administration steps may range from, for example, a few minutes to several hours to days, depending upon the properties of each therapeutic compound such as potency, solubility, bioavailability, plasma half-life and kinetic profile of the therapeutic compound, as well as depending upon the effect of food ingestion and the age and condition of the subject. Circadian variation of the target molecule concentration may also determine the optimal dose interval. The therapeutic compounds of the combined therapy whether administered simultaneously, substantially simultaneously, or sequentially, may involve a regimen calling for administration of one therapeutic compound by oral route and another therapeutic compound by an oral route, a percutaneous route, an intravenous route, an intramuscular route, or by direct absorption through mucous membrane tissues, for example. Whether the therapeutic compounds of the combined therapy are administered orally, by inhalation spray, rectally, topically, buccally (for example, sublingual), or parenterally (for example, subcutaneous, intramuscular, intravenous and intradermal injections, or infusion techniques), separately or together, each such therapeutic compound will be contained in a suitable pharmaceutical formulation of pharmaceutically-acceptable excipients, diluents or other formulations components.

The term "prevent" or "prevention," in relation to a type 1 diabetic disorder or disease, means no type 1 diabetic disorder or disease development if none had occurred, or no further type 1 diabetic disorder or disease development if there had already been development of the disorder or disease.

The term "suspend" or "suspending" or "suspending the onset of" in relation to a type 1 diabetic disorder or disease refers to increasing time to clinical onset of diabetes for a given subject or group of subjects. Diabetes or the onset of diabetes can be determined by any method known in the art. (See, for example, The American Diabetes Association at http://www.diabetes.org/homepage.jsp). Illustratively, onset of diabetes in a human subject will be determined on the basis of too-high levels of urine or serum glucose levels as compared to a normal subject by using, for example, a urine glucose level test or a fasting plasma glucose test, respectively. In the fasting plasma glucose test, a subject will fast overnight (for example, at least about 8, 12, 16, or 24 hours) and a sample of the subject's blood will be drawn in the morning. Typically, normal fasting plasma glucose levels are less than about 110 milligrams per deciliter (mg/dl). Fasting plasma glucose levels of more than about 126 mg/dl on two or more tests on different days indicate development of a type 1 diabetic disorder or disease. In another embodiment, onset of diabetes can be determined randomly by testing blood glucose levels taken shortly after eating or drinking. Blood glucose levels greater than about 200 mg/dl indicates diabetes, and can be confirmed with another test, such as, a fasting plasma glucose test or an oral glucose tolerance test, for example. In an oral glucose tolerance test, a subject undergoes a fast of at least about 8 to 16 hours and is then administered about 75 grams of glucose (or 100 grams for a pregnant women). Blood samples are taken over a period of about 2 to 3 hours. In a subject where blood glucose levels rise higher than normal (for example, blood glucose levels greater than 200 mg/dl between 0 to 2 hours, or greater than about 140 mg/dl at 2 hours) the subject is diagnosed with impaired glucose tolerance and may be at risk of developing diabetes or may be confirmed to have diabetes with additional testing. In another embodiment, a subject is confirmed to have diabetes when two or more diagnostic tests are done on different days that shows that blood glucose levels are higher than normal for the particular subject. The particular test used may vary to confirm the delay of onset of diabetes and will generally be interpreted on a subject-by-subject basis determined by those skilled in the art. For example, in an adult women, gestational diabetes may be diagnosed when one or more of the following results are positive: (i) a fasting (for example, at least 8 hours) blood glucose level greater than about 95 mg/dl; (ii) a one-hour glucose level greater than about 180 mg/dl; (iii) a two-hour glucose level greater than about 155 mg/dl; or (iv) a three-hour glucose level greater than about 140 mg/dl. Another test useful in the present invention commonly used by those skilled in the art to diagnose impaired glucose tolerance or diabetes is the glycated hemoglobin test, or A1C test.

The use of the term "about" in the present disclosure means "approximately," and illustratively, the use of the term "about" indicates that values slightly outside the cited values may also be effective and safe, and such dosages are also encompassed by the scope of the present claims.

The term "pharmaceutically-effective amount" in relation to the amount of an agent to treat type 1 diabetes means, consistent with considerations known in the art, the amount of a type 1 diabetic agent effective to elicit a pharmacologic effect or therapeutic effect (including, but not limited to, reducing and/or controlling hyperglycemia), without undue adverse side effects.

The term "treat" or "treatment" as used herein refers to any treatment of a disorder or disease associated with type 1 diabetes, and includes, but is not limited to, preventing the disorder or disease from occurring in a subject which may be predisposed to the disorder or disease, but has not yet been diagnosed as having the disorder or disease; inhibiting the disorder or disease, for example, arresting the development of the disorder or disease; relieving the disorder or disease, for example, causing regression of the disorder or disease; relieving the condition caused by the disease or disorder, for example, stopping the symptoms of the disease or disorder, and/or delaying the onset of the disease or disorder. For example, treatment of a subject include reducing blood glucose levels in a hyperglycemic subject, and/or maintaining acceptable control of blood glucose levels in the subject. Such treatment, prevention, symptoms and/or conditions can be determined by one skilled in the art and are described in standard textbooks.

In another embodiment of the present invention, the composition of the present invention comes in the form of a kit or package containing one or more of the compositions or therapeutic agents of the present invention. The composition containing the composition or therapeutic agent can be packaged in the form of a kit or package in which hourly, daily, weekly, or monthly (or other periodic) dosages are arranged for proper sequential or simultaneous administration. The present invention further provides a kit or package containing a plurality of dosage units, adapted for successive daily administration, each dosage unit comprising at least one of the compositions or therapeutic agents of the present invention. This drug delivery system can be used to facilitate administration of any of the various embodiments of the compositions and therapeutic agents of the present invention. In one embodiment, the system contains a plurality of doses to be to be administered daily or as needed for symptomatic relief. The kit or package can also contain agents utilized in combination therapy to facilitate proper administration of the dosage forms. The kit or package can also contain a set of instructions for the subject.

EXAMPLES

The present invention is further illustrated by the following examples, which should not be construed as limiting in any way. The materials and methods as used in the following experimental examples are described below.

Mice

NOD (H-2$^{g7}$) mice were purchased from Jackson Laboratories (Bar Harbor, Me.) and IL-10-deficient (IL-10$^{-/-}$) NOD mice were previously described (32) and are also available from Jackson Laboratories. All mice were maintained in an animal facility for the duration of experiments and the experimental procedures performed on these animal were carried out according to the guidelines of the institutional animal care committee.

Assessment of Diabetes

Mice are bled from the tail vein weekly and the blood samples are used to assess for both glucose content and anti-insulin antibodies. For measurement of glucose, a drop of blood is directly placed on a test strip and the glucose content is read using an Accu-Chek Advantage monitoring system (Roche Diagnostics, Indianapolis, Ind.). For detection of anti-insulin antibodies the blood is allowed to coagulate for 1 hour at room temperature and the serum is separated and used for ELISA. A mouse is considered diabetic when the blood glucose is above 300 mg/dl for two consecutive weeks.

Peptides

All peptides used in this study were purchased from Research Genetics, Inc. (Huntsville, Ala.) and purified by HPLC to >90% purity. INSβ peptide (Seq. I.D. No. 1 [SHLVEALYLVCGERG]) encompasses a diabetogenic epitope corresponding to amino acid residues 9-23 of the insulin β chain (30, 31). Hen egg lysozyme ("HEL") peptide (Seq. I.D. No. 2 [AMKRHGLDNYRGYSL]) encompasses a non-diabetogenic epitope corresponding to amino acid residues 11-25 of HEL. Both INSβ and HEL peptides are presented to T cells in association with I-A$^{g7}$ MHC class II molecules (30, 33). Other peptides that may be inserted within the variable region within the CDR region of an Ig and utilized for creating compositions for the treatment of type 1 diabetes as taught in the present invention are: GAD1 (Glutamic acid decarboxylase-65 also known as "GAD65"); corresponding to amino acid residues 524-543 of GAD 65 (Seq. I.D. No. 3 [SRLSKVAPVIKARMMEYGTT]) to create chimera Ig-GAD1; and 2) GAD2; corresponding to amino acid residues 206-220 of GAD 65 (Seq. I.D. No. 4 [TYEIAPVFVLLEYVT]); and other peptides derived from GAD65.

Other peptides derived from GAD or the human insulin protein (alpha and beta chains) are within the scope of the present invention. The peptides are often referred to herein as a "T cell receptor engaging determinant or epitope" in that they may work as an agonist or an antagonist or may interfere with the T cell receptor in another manner.

Ig Chimeras

Ig-INSβ is a chimera expressing INSβ peptide, which corresponds to amino acid residues 9-23 of insulin β chain. Construction of Ig-INSβ used the genes coding for the heavy and light chains of the anti-arsonate antibody, 91A3, according to the procedures described for the construction of Ig-PLP1 (18, 34). In brief, the 91A$_3$V$_H$ gene was subcloned into the EcoRI site of a pUC19 plasmid and used as template DNA in PCR mutagenesis reactions to generate 91A$_3$V$_H$ fragments carrying the INSβ (91A$_3$V$_H$-INSβ) sequence in place of the D segment within complementarity determining region 3 (CDR3). The 91A3V$_H$-INSβ fragment was then subcloned into an expression vector in front of the exons coding for the constant region of a BALB/c γ2b (18). This plasmid was then co-transfected into the non-Ig-producing SP2/0 myeloma B cell line with an expression vector carrying the parental 91A3 light chain. Transfectants producing Ig-INSβ were selected in the presence of geneticin and mycophenolic acid. Ig-HEL, which encompasses amino acid residues 11-25 of HEL, was constructed using the same 91A3 genes according to the procedure described for Ig-INSβ. Both chimeras are made of identical heavy and light chain but carry different peptides. Ig-W, the parental 91A3 Ig (encoded by wild-type genes) not encompassing any foreign peptide, has been described elsewhere (18). Large-scale cultures of transfectoma cells were carried out in DMEM media containing 10% iron-enriched calf serum (BioWhittaker, Walkersville, Md.). Purification of Ig-INSβ, Ig-HEL, and Ig-W was carried out on separate columns of rat anti-mouse-kappa chain mAb coupled to CNBr-activated 4B sepharose (Amersham Pharmacia Biotech, Piscataway, N.J.).

It is also within the scope of the invention that the immunoglobulin or portion thereof has more than one peptide linked to the immunoglobulin. Furthermore, the immunoglobulin, or a portion thereon, can be human or humanized, such as, for example, human IgG, such as IgG1, IgG2, IgG2a, IgG2b, IgG3, IgG4, IgGA, IgA1, IgA2, IgGE, IgD, IgE, or IgM. The Ig-P chimeras of the present invention may also comprise a pharmaceutically acceptable carrier.

Aggregation of the Ig Chimeras

The chimeras were aggregated by precipitation with 50%-saturated $(NH_4)_2SO_4$ as has been previously described (22). In brief, filtered 100% saturated $(NH_4)_2SO_4$ was added at an equal volume to the Ig chimera preparation. The mixture was incubated at 24° C. for 1 hour with gentle agitation every 20 minutes. Subsequently, the samples were spun down at 10,000 rpm, and the pellet was resuspended at 1 mg/ml in PBS. Electrophoresis on a 10% acrylamide gel confirmed that the Ig chimera preparation was in aggregate form. Since both Ig-INSβ and Ig-HEL derive from the same Ig backbone and thereby comprise identical IgG2b isotype, their Fc associated functions will be similar.

Radioimmunoassay (RIA)

Capture RIA was used to assess secretion of complete Ig-INSβ and Ig-HEL constructs from SP2/0 transfectants. Microtiter 96-well plates were coated with polyclonal rabbit anti-mouse-γ2b chain specific antibody (Zymed Laboratories, South San Francisco, Calif.) (2 μg/ml in PBS) overnight at 4° C. and then blocked with 2% BSA in PBS for 1 hour at room temperature. The plates were then washed three times with PBS and 100 μl/well of supernatant from SP2/0 cells growing in the presence of selective drugs was incubated for 2 hours at room temperature. After three washes with PBS, captured Ig-chimeras were revealed by incubation with $1 \times 10^5$ cpm/well $^{125}$I-labeled rat anti-mouse kappa mAb (ATCC, Rockville, Md.) for 2 hours at 37° C. The plates were then washed five times with PBS and counted using a Wallac LKB gamma counter.

Generation of T Cell Lines and Hybridomas

T cell lines: A T cell line specific for INSβ peptide was generated by immunizing NOD mice with 100 μg of INSβ peptide in 200 μl PBS/CFA (vol/vol) subcutaneously ("s.c.") in the footpads and at the base of each limb. After 10 days, the draining lymph nodes were removed, and T cells were stimulated in vitro for 2 rounds in the presence of irradiated (3000 rads), syngenic splenocytes, 5% T-Stim supplement (Collaborative Biomedical Products, Bedford, Mass.), and INSβ peptide (25 μg/ml). The culture media used to carry out these stimulations and other T cell activation assays in this study was DMEM supplemented with 10% FCS (Hyclone, Logan, Utah), 0.05 mM 2-mercaptoethanol, 2 mM glutamine, 1 mM sodium pyruvate, and 50 μg/ml gentamycin sulfate. NOD mice were also used for immunization with HEL peptide and generation of T cell line specific for HEL according to procedures similar to the INSβ specific line.

T cell hybridomas: A HEL-specific T cell line was fused with the αβ TCR negative thymoma BW1100 (ATCC) using polyethylene glycol 4000 (Sigma, St. Louis, Mo.). Hybrids were then selected by supplementing the culture media with hypoxanthine-azaserine (Sigma). Resulting hybridomas were then screened for reactivity to HEL peptide by testing for production of IL-2 in the supernatant following stimulation with irradiated (3000 rads) splenocytes in the presence of 15 μg/ml HEL peptide. Positive hybridomas were then cloned by limiting dilution and used to assess presentation of HEL peptide and Ig-HEL chimera.

Detection of Insulin Autoantibodies.

Detection of insulin autoantibodies ("IAA") in the serum of NOD mice was carried out by ELISA as follows: microtiter plates number 3369 (Corning Inc, Corning, N.Y.) were coated with 50 μl sodium bicarbonate solution (pH 9.6) containing 10 μg/ml porcine insulin (Sigma, Saint Louis, Mo.) for 16 hours at 4° C. The plates were then washed 3 times with PBS-0.05% Tween-20 and free plastic sites were saturated by incubation with 2.5% Casein (in 0.3M NaCl pH 7) for 2 hours at RT. Subsequently, serum samples (1/200 dilutions) were added and the plates were incubated for 16 hours at 4° C. Biotin-conjugated rat anti-mouse kappa mAb (100 μl at 1 μg/ml) was added and the plates were incubated for 1 hour at RT. Bound anti-mouse Kappa mAb was revealed by incubation with a casein solution containing 2.5 mg/ml avidin peroxidase for 30 min at RT followed by addition of ABTS substrate. The samples were read at 405 nm on a Spectramax 190 (Molecular Devices, Sunnyvale, Calif.)

Regimens for Suppression of Diabetes

Treatment of IAA-positive NOD mice with Ig-INSβ: Preliminary studies were carried out and indicated that seroconversion to IAA-positive occurs most frequently between the ages of 8 and 12 weeks. Mice are given weekly intraperitoneal injections of soluble or agg Ig-INSβ or Ig-HEL beginning the week of seroconversion. The mice were given either 2 or 3 injections 7 days apart of Ig chimera in 300 µl saline solution. Beginning at week 12 of age, the mice were tested weekly for blood glucose up to week 30 unless previously diagnosed diabetic.

Treatment of NOD mice with Ig-INSβ at the pre-insulitis stage: The mice were given a weekly i.p. injection of 300 µg Ig-INSβ or Ig-HEL in 300 µl saline beginning at week 4 for a total of 3 injections. Beginning at week 12 of age, the mice were tested weekly for blood glucose up to week 30 unless previously diagnosed diabetic.

Detection of Cytokines in Cell Cultures

Detection of IL-10 and IFNγ was performed according to BD Pharmingen's standard protocol. The capture Abs were as follows: rat anti-mouse IL-10, JES5-2A5 and rat anti-mouse IFNγ, R4-6A2. The biotinylated anti-cytokine Abs were as follows: rat anti-mouse IL-10, JES5-16E3 and rat anti-mouse IFNγ, XMG1.2. Both antibodies were purchased from BD Pharmingen (San Diego, Calif.). ELISA for the detection of active TGFβ was preformed using the human $TGF\beta_1$ DuoSet kit (R&D systems, Minneapolis, Minn.) according to the manufacturer's instructions. Bound TGFβ was revealed using the TMB microwell peroxidase substrate system (Kirkegaard & Perry Laboratories, Gaithersburg, Mass.). All assays were read on a SpectraMAX 190 counter. Graded amounts of recombinant mouse IFNγ, IL-10, and TGFβ were included in all experiments for construction of standard curves. The cytokine concentration in culture supernatants was interpolated from the linear portion of the standard curve.

Measurement of T Cell Responses

Responses of T cell lines: Purified bulk, dendritic cells ("DCs") were plated at $5\times10^4$ cells/well/50 µA and incubated with graded amounts of soluble or agg Ig-chimeras (100 µl/well) for 1 hour. Subsequently, peptide-specific T cells ($5\times10^4$ cells/well/50 µl) were added, and the culture was continued for 24 h. Detection and quantification of cytokines were assessed by ELISA from 100 µl of culture supernatant as described above.

Responses of NOD splenic T cells upon treatment with Ig-INSβ: Splenic cells ($1\times10^6$ per well) which include both T lymphocytes and APCs were incubated with 30 µg INSβ peptide and T cell responses were analyzed. Cytokines were measured by ELISA after 48 hours of incubation as described above and proliferation was assessed by [$^3$H] thymidine incorporation after 3 days. In this proliferation assay the cells were incubated in 96-well flat bottom plates with or without the stimulator for 3 days and 1 µCi [$^3$H] thymidine was added per well, during the last 14.5 h of stimulation. The cells were then harvested on a Trilux 1450 Microbeta Wallac Harvester and incorporated [$^3$H] thymidine was counted using the Microbeta 270.004 software (EG&G Wallac INC, Gaithersburg, Md.). A control media with no stimulator was included and used as background.

Isolation of Splenic Dendritic Cells

Splenic DCs were purified according to the standard collagenase/differential adherence method (35). Briefly, the spleen was disrupted in a collagenase solution, and isolated DCs floated on a dense BSA gradient. Subsequently, the cells were allowed to adhere to petri dishes for 90 minutes at 37° C., washed, and incubated overnight. The DCs are then harvested and further purified on anti-CD11c coupled microbeads according to Miltenyi's instructions.

Stimulation of Cytokine Production by Dendritic Cells

Purified splenic CD11e DCs from NOD mice were plated with graded amounts of soluble or agg Ig chimeras, and the culture was then incubated for 24 h with or without specific T cells. Detection and quantification of cytokines was then assessed by ELISA from 100 µl of culture supernatant as described above.

Isolation of Islet-Infiltrating Lymphocytes

Islet-infiltrating cells were derived from 14 week old female NOD mice by collagenase digestion as previously described (36). Briefly, pancreata were collected in a PBS solution containing 5% FCS and 1% glucose, finely minced, and digested in a collagenase type IV (Invitrogen Corp., Carlsbad, Calif.) solution supplemented with 15% FCS for 8 min at 37° C. Islets were then pressed through a 100 µm metal sieve and successively filtered through 70 µm and 40 µm nylon screens to recover infiltrating cells. Viability of the cells was determined by trypan blue exclusion.

Example 1

Expression of INSβ and HEL Peptides on Ig Molecules Drives Efficient Presentation to T Cells Recent studies have revealed that mice with an ongoing EAE ameliorate their disease when treated with chimeric Igs expressing myelin epitopes (20, 22, 23). This investigation seeks to determine whether similar delivery of a diabetogenic peptide on Igs could inhibit IDDM in the NOD mouse. The $I-A^{g7}$-restricted INSβ peptide defined to be associated with the development of diabetes in the NOD mouse (37, 38) was selected for expression on Igs to generate an Ig-INSβ chimera suitable for evaluation against diabetes. HEL peptide, which is presented by $I-A^{g7}$ MHC class II molecules without causing diabetes (30), was used to generate an Ig-HEL chimera to serve as a control. Accordingly, INSβ and HEL nucleotide sequences were separately inserted into the CDR3 of the 91A3 heavy chain by PCR mutagenesis (18) and the resulting chimeric heavy chain genes were analyzed by DNA sequencing (see "Materials and Methods").

The results presented in FIG. 1 show the nucleotide sequences of these inserts as well as the flanking regions surrounding them. The top panel shows a comparison of the nucleotide sequence of the parental $91A_3V_H$ gene to the sequences of the chimeric $91A_3V_H$-INSβ and $91A_3V_H$-HEL. Both chimeric $91A3V_H$-INSβ and $91A3V_H$-HEL fragments were subcloned into an expression vector in front of the exons coding for the constant region of a BALB/cγ2b. The plasmids were then separately co-transfected into the non-Ig-producing SP2/0 myeloma B cell line with an expression vector carrying the parental 91A3 light chain. Transfectants producing Ig-INSβ were selected in the presence of geneticin and mycophenolic acid as described in the "Materials and Methods" ("Ig Chimeras") (18). In the lower panel detection of secreted chimeric Ig in the supernatant from transfectoma cells was carried out by incubation of supernatant of Ig-INSβ, Ig-HEL or Ig-W transfectants on microtiter plates coated with rabbit anti-mouse γ2b-chain specific antibody and revelation of captured Ig-chimeras with [$^{125}$I]-labeled rat anti-mouse kappa light chain mAb. Each bar represents the mean±SD of triplicates.

The data indicate that the INSβ nucleotide sequence was fully inserted in place of the D segment. The flanking regions surrounding INS are identical to those regions flanking the D segment within the parental heavy chain indicating that the INSβ nucleotide sequence was inserted in the correct reading frame. Similar results were obtained with HEL peptide indicating that a full nucleotide sequence of HEL peptide was incorporated in the correct reading frame. Subsequently, these chimeric heavy chain genes were subcloned into a pSV2 expression vector and separately co-transfected with the parental 91A3 kappa light chain gene into the non-Ig-secreting myeloma B cell line SP2/0 (18) and as taught in the "Materials and Methods" ("Ig Chimeras").

Using selective drugs, the wells with cell growth were identified visually, and their supernatants were tested for the presence of Igs. As depicted in the lower panel of FIG. 1, supernatant from a representative Ig-INSβ transfectant incubated on plates coated with anti-γ2b antibody bound a rat anti-mouse kappa light chain mAb, as did Ig-W, the parental 91A3 antibody with an intact CDR3 domain indicating that the 91A3-INSβ chimeric heavy chain paired with the parental light chain and formed a complete Ig-INSβ molecule. Similarly, a representative supernatant from a 91A3-HEL transfectant showed significant binding of the anti-light chain antibody indicating that insertion of the HEL peptide within the heavy chain variable region did not alter pairing with the parental light chain and a complete Ig-HEL molecule was produced.

Example 2

Ig-INSβ is Processed Properly and Generates an INSβ Peptide that could be Presented to T Cells The next question to address was whether Ig-INSβ is processed properly and generates an INSβ peptide that could be presented to T cells. To test this premise, the chimera was purified from the supernatant of large-scale cultures by affinity chromatography and assayed for presentation using an INSβ-specific T cell line that has been generated in NOD mice by immunization with INSβ peptide (see "Materials and Methods"). Similarly, to ensure that HEL peptide could be processed from Ig-HEL and presented to T cells, an HEL-specific hybridoma was generated by fusing the HEL-specific short-term T cell line with the αβ-T cell receptor (αβ-TCR)-negative thymoma BW1100 (see "Material and Methods").

Presentation of Ig-INSβ chimera to specific T cells was then determined. Irradiated (3000 rads) NOD splenocytes (5×10$^5$ cells/50 µl/well) were incubated with 100 µl antigen and one hour later T cells (5×10$^4$ cells/well/50 µl) specific for either INSβ (FIG. 2(a)-2(b)) or HEL (FIG. 2(c)-2(d)) peptide were added. For presentation of INSβ peptide and Ig-INSβ (FIGS. 2(a) and 2(b) respectively), the activation was assessed by [$^3$H] thymidine incorporation since the T cells were from a line. Accordingly, 1 µCi [$^3$H]thymidine per well was added during the last 14 hours of a 3-day incubation period and the cells were harvested, and the radioactivity counted. For presentation of HEL peptide (FIG. 2(c)) and Ig-HEL (FIG. 2(d)), T cell activation was assessed by measuring IL-2 production as the HEL-specific cells were from a hybridoma. Accordingly, after 24 hours incubation IL-2 was measured in 100 µl supernatant by ELISA. In this assay the peptides were used at 10 µM concentration and the Ig-chimeras at 1 µM. Each point or bar represents the mean of triplicates.

Figure 2:
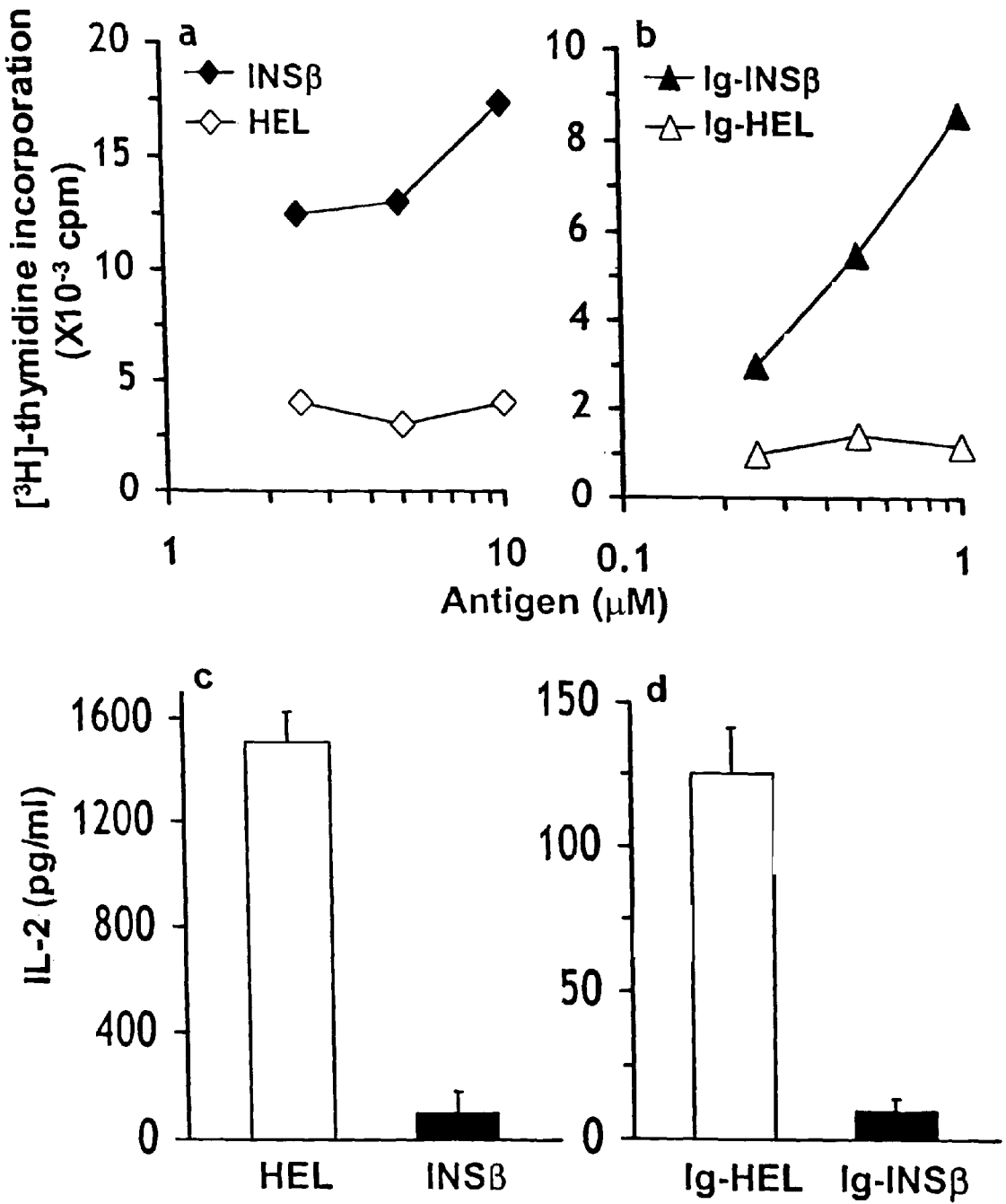
FIG. 2 demonstrates that the INSβ-specific T cell line proliferated significantly upon incubation with irradiated NOD splenic APCs and INSβ peptide (FIG. 2(a)), or Ig-INSβ (FIG. 2(b)), indicating that Ig-INSβ is taken up by the APCs and an INSβ peptide is generated and presented to T cells.

As indicated in FIG. 2, the INSβ-specific T cell line proliferated significantly upon incubation with irradiated NOD splenic APCs and INSβ peptide (FIG. 2(a)), or Ig-INSβ (FIG. 2(b)) indicating that Ig-INSβ is taken up by the APCs and an INSβ peptide is generated and presented to T cells. HEL peptide and Ig-HEL, although able to stimulate the HEL-specific hybridoma as measured by IL-2 production (FIGS. 2(c) and 2(d)), were unable to induce proliferation of the INSβ-specific line indicating that presentation of INSβ and Ig-INSβ is specific. The above described results demonstrate that INSβ and HEL peptide expressed on Igs are functional and suitable for evaluation of suppression of diabetes.

Example 3

Insulin-Specific Autoantibodies can Serve as a Marker for Early Development of Diabetes Gender study of the incidence of diabetes in our NOD colony indicated that 38% of male NOD mice develop spontaneous diabetes by the age of 26 weeks. However, female NOD mice have shown a greater susceptibility for the disease and 80% developed spontaneous diabetes at week 26 of age. This is in good agreement with previous reports and suggests that the use of female mice would be more suitable for our investigation.

Recently, it has been shown that IAA can be used as a marker for prediction of type I diabetes in children and young NOD mice (39, 40). This is advantageous as it targets intervention prior to significant destruction of β cells without compromising the accuracy of the study. Therefore, it was decided to develop a chart to include only IAA-positive mice to assess the ability of Ig-INSβ for suppression of diabetes. Accordingly, a group of 70 NOD female mice was subject to weekly testing for IAA beginning at week 6 through week 12 of age and the IAA-positive mice were monitored for blood glucose thereafter and up to 30 weeks.

Figure 3:
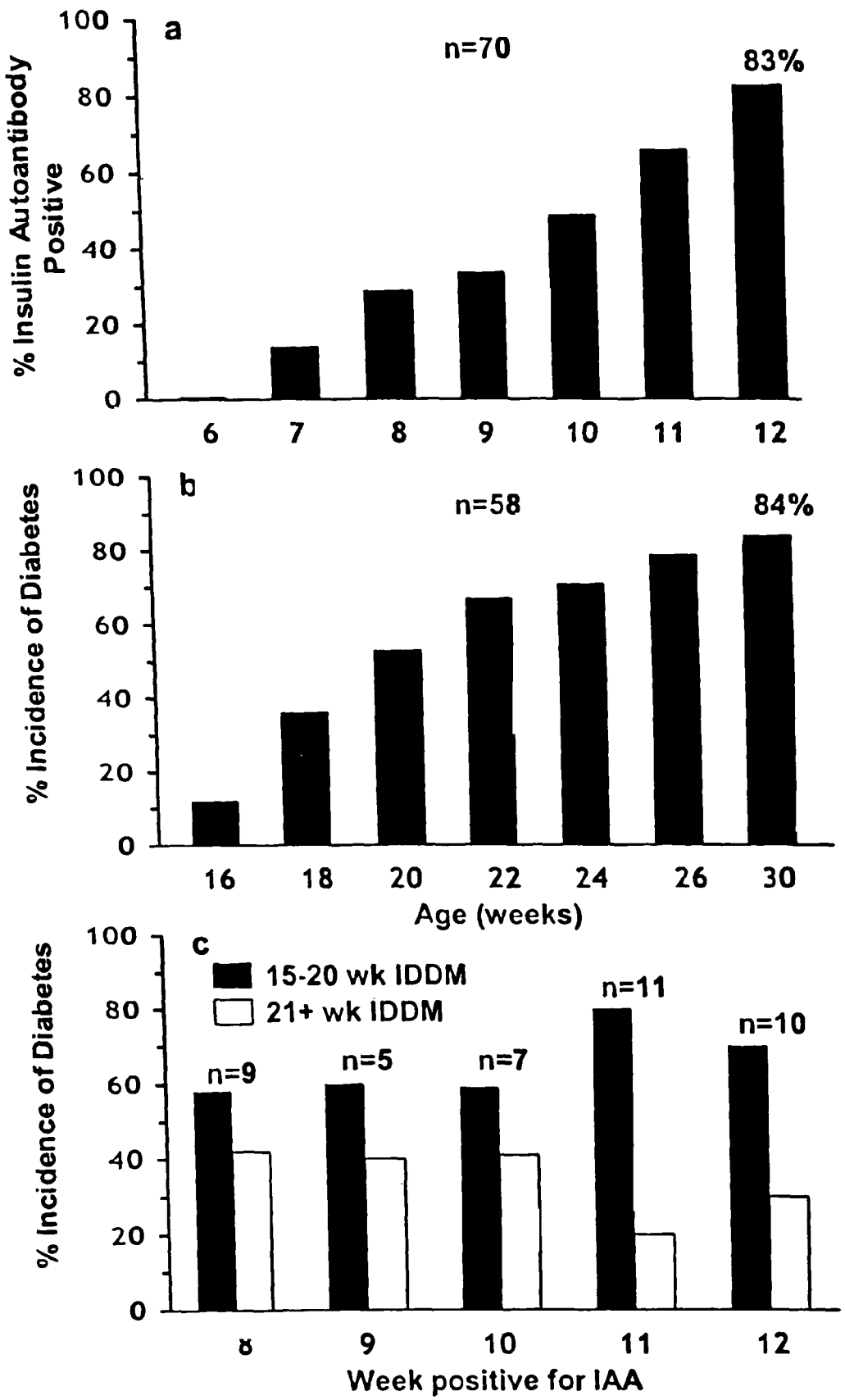
FIG. 3 shows that insulin-specific autoantibodies can serve as a marker for early development of diabetes.

In FIG. 3(a), 70 adult female NOD mice were bled weekly starting at the age of 6 weeks and their serum samples were tested for IAA at a 1/200 dilution by ELISA as described in the "Materials and Methods" section. A sample is considered IAA-positive when the OD$_{405}$ is >0.2. The cutoff of 0.2 was chosen because serum samples from 10 SJL mice, non-prone to diabetes development and presumably do not produce insulin specific autoantibodies, never exceeded 0.2 OD$_{405}$. Among the 70 mice tested, 58 (83%) have shown an IAA-positive result. In FIG. 3(b), the 58 mice that tested IAA-positive by week 12 were subjected to weekly measurement of blood glucose beginning at week 12 continuing through week 30. Among the 58 IAA-positive mice, 49 (84%) become diabetic by age 30 weeks. FIG. 3(c) shows the percent incidence of early (15-20 weeks of age) and delayed (21 to 30 weeks of age) diabetes for mice developing IAA at the indicated weeks. n indicates the number of mice per group.

As indicated in FIG. 3(a), the appearance of IAA begins at week 7 and by 12 weeks of age 58 among the 70 mice tested (83%) had become IAA-positive. Furthermore, among the 58 IAA-positive mice, 84% had become diabetic by 30 weeks of age (FIG. 3(b)) indicating that IAA can serve as a marker for the development of type I diabetes in female NOD mice. Interestingly, a significant percentage (60%) of the mice that became IAA-positive at week 8, 9, or 10 manifested diabetes at the age of 15 to 20 weeks and such early incidence rose to 80% for the mice who developed IAA at week 11 of age (FIG. 3(c)). Therefore, these results demonstrate suggest that development of IAA between the age of 8 to 11 weeks can serve as a marker for the development of diabetes at the early age of 15 to 20 weeks.

Example 4

Soluble Ig-INSβ Delays Diabetes when Administered into Mice Upon IAA Seroconversion Although infiltration of the pancreatic islets with inflammatory cells occurs long before hyperglycemia, pancreatic biopsy for histologic analysis represents an impractical approach for prediction of the onset of diabetes. Detection of IAA in blood samples is practical and has proven reliable for the prediction of early diabetes onset in the NOD mouse (39, 40). Thus, the IAA marker was used for evaluation of Ig-INSβ for suppression of diabetes before onset of hyperglycemia. Accordingly, NOD mice were tested for the presence of IAA and those who seroconverted at the age of 8 to 11 weeks were given soluble Ig-INSβ in saline on the week of seroconversion and thereafter as indicated, and monitored for blood glucose up to week 26 of age. Specifically, groups of female NOD mice (10 per group) positive for IAA between the age of 8 and 11 weeks were given an intraperitoneal ("i.p.") injection of 100 μg (a), 200 μg (b), or 300 μg (c) of either soluble Ig-INSβ (black bars) or soluble Ig-HEL (hatched bars) on the week of seroconversion. All groups were given an additional injection of the same amount 7 days later and the mice in FIG. 4(c) received a third injection on day 14 after seroconversion. A seventh group did not receive any injection (Nil: open bars) and was incorporated in the three panels to serve as a control. The percentage incidence of diabetes is shown in each of the groups at week 19 and 26 of age in FIGS. 4(a)-4(c).

As can be seen in FIG. 4(a), two doses of 100 μg soluble Ig-INSβ had no significant delay on early onset diabetes and most of the animals became diabetic by week 26 of age. When two doses of 200 μg soluble Ig-INSβ were applied (FIG. 4(b)), the onset of diabetes was delayed and only 30% of the mice become diabetic by week 19 relative to 50% in the untreated group. Complete prevention was not achieved and by week 26 most of the soluble Ig-INSβ-treated animals developed diabetes. The delay of diabetes is antigen-specific as Ig-HEL had no significant delay or protection against diabetes. Increasing the dose to 300 μg per injection and giving a total of 3 injections delayed the early-onset diabetes significantly as only 20% of the mice developed diabetes by week 19 relative to 50% in the untreated group (FIG. 4(c)). Moreover, 50% of the soluble Ig-INSβ treated mice remained free of disease by week 26 of age while only 20% in the untreated group had no diabetes. The control Ig-HEL had no significant delay or protection against early or delayed diabetes.

Example 5

Administration of Agg Ig-INSβ into NOD Mice Induces Antigen-Specific Non-Proliferative T Cells Producing Both IL-10 and TGFβ

Aggregation of Igs confers Fc associated functions such as cross-linking of FcγRs and activation of complement (41, 42). It has been previously shown that aggregation of Ig-myelin chimeras using the same IgG2b backbone as Ig-INSβ and Ig-HEL cross-links FcγRs on APCs and induces the production of IL-10 by both dendritic cells and macrophages (22, 23). In addition, while soluble Ig-myelin chimeras suppressed relapses with little effect on the initial severe phase of EAE, agg chimeras induced full and expeditious recovery from the initial paralytic phase and the relapses (20, 22). Neutralization of endogenous IL-10 by administration of anti-IL-10 antibody during treatment with the agg Ig-myelin chimeras restored disease severity (22). These results indicated that cross-linking of FcγRs and IL-10 production by APCs potentiate the modulatory function of Ig-myelin chimeras and promote effective suppression of EAE (20, 22). Such effectiveness may be due to synergy between endogenous IL-10 and myelin-peptide presentation with minimal costimulation (20). However, since IL-10 can serve as a growth factor for the development of regulatory T cells (43, 44), there may be induction of such cells that could support continuous production of IL-10 and provide additional modulatory functions against pathogenic T cells. To test whether similar effects could develop in the NOD system, Ig-INSβ was aggregated (see "Aggregation of Ig Chimeras" in "Materials and Methods") and tested for induction of IL-10 by APCs, down-regulation of INSβ-specific T cell line in vitro and induction of IL-10 producing T cells in vivo.

In FIG. 5a, purified NOD splenic DCs ($5 \times 10^4$ cells/well) were incubated with graded amounts of agg Ig-INSβ (closed circles) or soluble Ig-INSβ (open circles) and production of IL-10 was measured by ELISA 24 hours later. For down-regulation of INSβ-specific T cells (FIGS. 5b-5d), purified NOD splenic DCs ($5 \times 10^4$ cells/well) were incubated with graded amounts of agg Ig-INSβ (FIG. 5b) or soluble Ig-INSβ (FIG. 5c) for 1 h. Subsequently, the INSβ-specific T cell line TCL-INSβ-C1 ($0.2 \times 10^5$ cells/well) was added and incubation was continued for an additional 24 h. IL-10 (closed diamonds) and IFNγ (open diamonds) production in the same culture wells were then measured by ELISA from 100 μl of culture supernatant. Each point represents the mean of triplicate wells.

In FIG. 5d, the assay was carried out in the absence (closed bars) or presence (open bars) of 40 μg/ml anti-IL-10 antibody or isotype control, rat IgG (hatched bars) with three different concentrations of agg Ig-INSβ. Each bar represents the mean±SD of triplicate wells.

The data shows that agg Ig-INSβ, which encompasses identical IgG2b isotype as the Ig-myelin chimeras, induced IL-10 production by DCs (FIG. 5a). Soluble Ig-INSβ, however, was unable to trigger IL-10 production by the same DCs indicating that cross-linking of FcγRs is required for cytokine production. Moreover, IL-10, produced by the DCs upon presentation of agg Ig-INSβ, displayed down-regulatory functions on the activation of specific T cells engaged to the DCs through INSβ peptide. Indeed, when INSβ-specific T cells were incubated with DCs and agg Ig-INSβ, the secretion of IFNγ by the T cells decreased as production of IL-10 by the DCs increased (FIG. 5b). Such down-regulation of IFNγ did not occur with soluble Ig-INSβ which did not induce IL-10 secretion by the DCs (FIG. 5c). Neutralization of IL-10 during stimulation with agg Ig-INS/3 restores IFNγ production by the T cells (FIG. 5d).

Overall, these results indicate that agg Ig-INSβ drives both IL-10 production and peptide presentation by APCs which support down-regulation of INSβ-specific T cells.

Example 6

Agg Ig-INSβ Reduces Th1 Responses but Supports Production of IL-10 and TGFβ Upon Administration into NOD Mice Since IL-10 has been defined to function as a growth factor for the development of regulatory T cells (45, 46) that produce IL-10 (43, 47), agg Ig-INSβ (which triggers production of IL-10 by APCs) was tested for stimulation of non-proliferative cytokine producing T cells in vivo. Accordingly, splenic cells from mice given agg Ig-INSβ on week 4, 5 and 6 were harvested on week 12 and tested for proliferation and cytokine production upon in vitro stimulation with INSβ peptide. The rationale for testing the cells on week 12, rather than 10 days after completion of the treatment, is related to the fact that Ig-INSβ was injected without adjuvants and accumulation of suppressor cells may take a longer period of time. In addition, tolerization of pathogenic T cells needs to be advanced to minimize residual responses.

A Group of 5 untreated female NOD mice (gray bars, see FIG. 6) as well a group of 5 mice recipient of 300 µg agg Ig-INSβ at week 4, 5 and 6 of age (black bars, see FIG. 6) were sacrificed at 12 weeks and their splenic proliferative and cytokine responses were measured. In FIG. 6(a), pooled splenocytes ($1\times10^6$ cells/well) from 5 mice were stimulated with 30 µg/ml INSβ peptide for 72 h and proliferation was assessed as described in the "Materials and Methods" section. In FIGS. 6(b)-6(d), pooled splenocytes were stimulated with INSβ peptide for 48 h and cytokine production was assayed by ELISA using 100 µl of supernatant. Each bar represents the mean of triplicate wells.

The results illustrated in FIGS. 6(a)-6(d) indicate that proliferation is reduced in mice given Ig-INSβ relative to untreated animals and IFNγ has begun to decrease most likely due to down-regulation of diabetogenic T cells. Furthermore, an increase in IL-10 production accompanied by a selective secretion of TGFβ has been observed in the mice given agg Ig-INSβ relative to untreated mice. Overall, these results indicate that agg Ig-INSβ induces antigen-specific non-proliferative T cells producing both IL-10 and TGFβ.

Example 7

Agg Ig-INSβ does not Delay Diabetes when Administered into NOD Mice Upon IAA Seroconversion As agg Ig-INSβ induced IL-10 by APCs and stimulated T lymphocytes producing suppressive cytokines, it was expected the chimeras to be effective against diabetes in IAA-positive mice. Surprisingly, the results illustrated in FIG. 7 point to a different outcome.

Groups of female NOD mice (10 per group) positive for IAA between the age of 8 and 11 weeks were given an intraperitoneal injection of 100 µg [FIG. 7(a)], 200 µg [FIG. 7(b)], or 300 µg [FIG. 7(c)] of either agg Ig-INSβ (black bars) or agg Ig-HEL (hatched bars) on the week of seroconversion. All groups were given an additional injection of the same amount 7 days later and the mice in FIG. 7(c) received a third injection on day 14 after seroconversion. A seventh group did not receive any injection (Nil: open bars) and was incorporated in the three panels to serve as a control. FIGS. 7(a)-7(c) show the percentage incidence of diabetes in each of the groups at week 19 and 26 of age.

Testament with 2 doses of 100 µg agg Ig-INSβ did not delay the onset of early diabetes and consequently, no prolonged protection against the disease was observed. Increasing the dose to 200 µg per injection also did not induce significant delay of the onset of early diabetes and most of the mice developed hyperglycemia by week 26 of age. Injection of 300 µg agg Ig-INSβ once a week for 3 consecutive weeks did not significantly delay the onset of early diabetes and thus no long term protection against the disease had occurred.

Example 8

Figure 8:
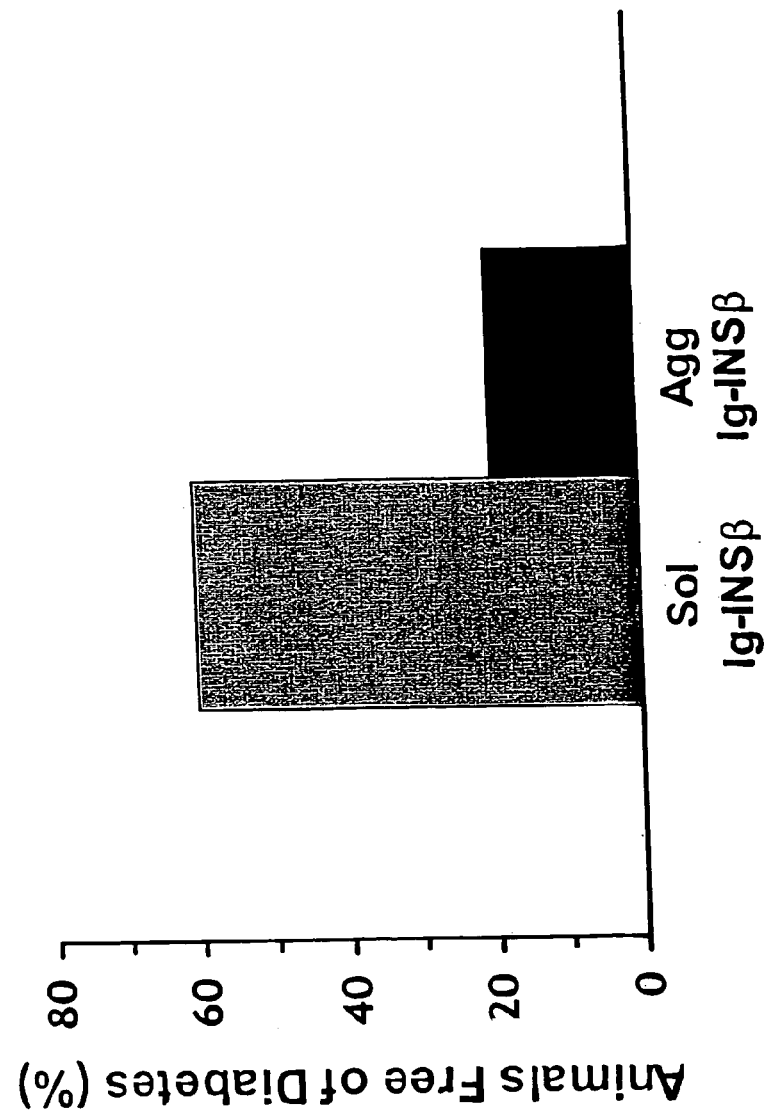
FIG. 8 shows that the soluble form of Ig-INSβ is much more effective than the aggregated form in the suppression of diabetes.

The Soluble Form of Ig-INSβ is Much More Effective than the Aggregated Form in the Suppression of Diabetes in IAA-Positive Mice As shown in FIG. 8, the bars represent the percentage of NOD mice that remained free of early (19 weeks) diabetes upon treatment with either agg Ig-INSβ or soluble Ig-INSβ. These percentages were generated according to the following formula: number of disease free animals in treated groups minus the number of disease free mice in the untreated group over the number of diabetic animals in the untreated group. These results were generated from the comparison of the mice recipient of 3 injections of 300 µg soluble Ig-INSβ (FIG. 4c) or agg Ig-INSβ (FIG. 7c).

These results are similar to those obtained with the control Ig-HEL. Overall, aggregated Ig-INSβ had little effect in delaying the onset of early or delayed diabetes. In fact, comparison of the soluble and aggregated forms of Ig-INSβ for suppression of diabetes after IAA seroconversion clearly shows that soluble Ig-INSβ significantly delays the onset of early diabetes and 60% of the mice were free of disease on week 19 (FIG. 8). In contrast, the aggregated form of Ig-INSβ, which brings IL-10 into the mechanism, had no statistically significant effect even in suppression of early diabetes.

Example 9

Agg Ig-INSβ is More Effective than Soluble Ig-INSβ in Delaying the Onset of Diabetes When Administered at the Pre-Insulitis Stage IL-10 has been shown to display contrasting effects on diabetes depending on the mode of delivery to the target cells (24-26). Similarly, IL-10-IL-10R interactions showed differential regulation of diabetes in young versus older animals (28). Since agg Ig-INSβ induces IL-10 production by APCs but did not suppress diabetes in IAA-positive animals while soluble Ig-INSβ, which does not induce IL-10 production, delayed diabetes, it was decided to investigate whether such differential effect on diabetes manifest when the chimeras are administered at the pre-insulitis stage.

Accordingly, NOD mice were given an injection of 300 µg of either agg or soluble Ig-INSβ at the age of 4 weeks and two additional injections (300 µg) at weeks 5 and 6, respectively, and the animals were monitored for blood glucose weekly up to week 26 of age. Groups of female NOD mice (10 per group) were given an i.p. injection of a saline solution containing 300 µg of soluble Ig-INSβ or agg Ig-INSβ (black bars), or Ig-HEL (hatched bars) at 4, 5 and 6 weeks of age (FIGS. 9(a)-9(b)). A fifth group that did not receive any injection (Nil: open bars) was included for control purposes. The mice were then monitored for blood glucose weekly up to 30 weeks of age. The percentage incidence of diabetes is shown in each of the five groups at week 16, 20 and 26 of age.

As can be seen in FIG. 9, soluble delayed the onset of diabetes and no animals had hyperglycemia by week 16 of age. Such delay persisted until week 20 but most of the mice developed diabetes by week 26. No such delay was observed with soluble Ig-HEL indicating that the effect on diabetes by Ig-INSβ is antigen specific. Surprisingly, however, agg Ig-INSβ delayed diabetes in all mice except 1 up to week 20 and such delay remained significant by week 26 where only 30 percent of the mice had high blood glucose while 80% of the untreated mice became diabetic (FIG. 9b). It is worth noting that Ig-HEL which induces IL-10 production by APCs displayed significant delay of diabetes up to week 20 possibly due to IL-10 bystander suppression (FIG. 9b).

These results indicate that agg Ig-INSβ is effective in delaying the onset of diabetes when administered at the pre-insulitis stage and suggest that IL-10 displays a down-regulatory function at this stage.

Example 10

Administration of Agg Ig-INSβ into IL-10$^{-/-}$ NOD Mice at the Pre-Insulitis Stage does not Delay Onset of Diabetes The role of agg Ig-INSβ-induced IL-10 on the suppression of diabetes became evident when IL-10$^{-/-}$ mice did not delay their diabetes onset upon treatment with agg Ig-INSβ while IL-10$^{+/+}$ did. Groups (10 mice per group) of female wild type (IL-10$^{+/+}$) and IL-10$^{-/-}$ NOD mice were given i.p. 300 μg of agg Ig-INSβ on week 4, 5 and 6 of age and monitored for blood glucose weekly. Shown is the percentage incidence of diabetes in both IL-10$^{-/-}$ and IL-10$^{+/+}$ mice at week 12, 16 and 20 of age after receiving the injections of agg Ig-INSβ. The results emphasize the importance of IL-10 on the suppression of diabetes in the preinsultits stage (see FIG. 10).

Example 11

Splenic and Islet Diabetogenic T Cells Develop Opposite Responses Against Agg Ig-INSβ

In 4 week old mice, islet infiltration has not taken place and most of the diabetogenic T cells remain peripheral while in IAA-positive mice, which would have reached the age of 14 weeks by completion of treatment with Ig-INSβ, insulitis would be advanced and most of the diabetogenic T cells would have infiltrated the islets (4). Thus, the difference in the delay of diabetes by agg Ig-INSβ in young versus IAA-positive mice may be due to a variable susceptibility to IL-10 of islet versus peripheral T cells.

To test this premise, splenic and islet cells from 14 week old mice were stimulated with agg Ig-INSβ, which induces IL-10 production by the presenting APCs and secretion of IFNγ was measured. Splenic (a) and islet (b) cells (5×10$^5$ cells/well) from 14 week old female NOD mice were stimulated with the indicated antigen in the presence or absence of 1 ng of rIL-10 for 24 hours. The supernatant (100 μl/well) was used to measure IFNγ by ELISA as indicated in "Materials and Methods". INSβ peptide was used at 18 μM and agg and soluble Ig-INSβ chimeras were used at 1 μM concentration. Each bar represents the mean±SD of triplicate wells for splenocytes and duplicate wells for islet cells.

As can be seen in FIG. 11, both splenic and islet T cells developed IFNγ responses upon stimulation with INSβ or soluble Ig-INSβ. However, stimulation with agg Ig-INSβ reduced IFNγ response by splenic T cells but enhanced the islet T cell response significantly. Similar effects were observed when the cells were stimulated with soluble Ig-INSβ or INSβ peptide in the presence of IL-10. These results indicate that islet and peripheral INSβ-specific T cells display differential susceptibility to IL-10.

Example 12

Sustained Administration of Soluble Ig-INSβ to Female NOD Mice after IAA Seroconversion Delays Onset of Diabetes A study was performed to assess the impact of sustained administration of soluble Ig-INSβ or Ig-HEL to female NOD mice that had previously undergone IAA seroconversion. Groups (n=10) of female NOD mice between the ages of 7 and 11 and positive for IAA were given a weekly interperitoneal injection of 300 μg of soluble Ig-INSβ or Ig-HEL beginning on the week of seroconversion and continuing until week 12 post-seroconversion. For mice that seroconverted on week 7, each mouse received an injection on weeks 7, 8, 9, 10, 11, and 12, and biweekly thereafter; for mice that seroconverted on week 8, each mouse received an injection on weeks 8, 9, 10, 11, and 12, and biweekly thereafter; for mice that seroconverted on week 9, each mouse received an injection on weeks 9, 10, 11, and 12, and biweekly thereafter; for mice that seroconverted on week 10, each mouse received an injection on weeks 10, 11, and 12, and biweekly thereafter; and for mice that seroconverted on week 11, each mouse received an injection on weeks 11 and 12, and biweekly thereafter. Subsequent to week 12 post-seroconversion, each mouse received an injection of 300 μg of soluble Ig-INSβ or Ig-HEL every 2 weeks until the mouse reached the age of 26 weeks. A third, control group received no injections throughout the duration of the study.

Figure 12:
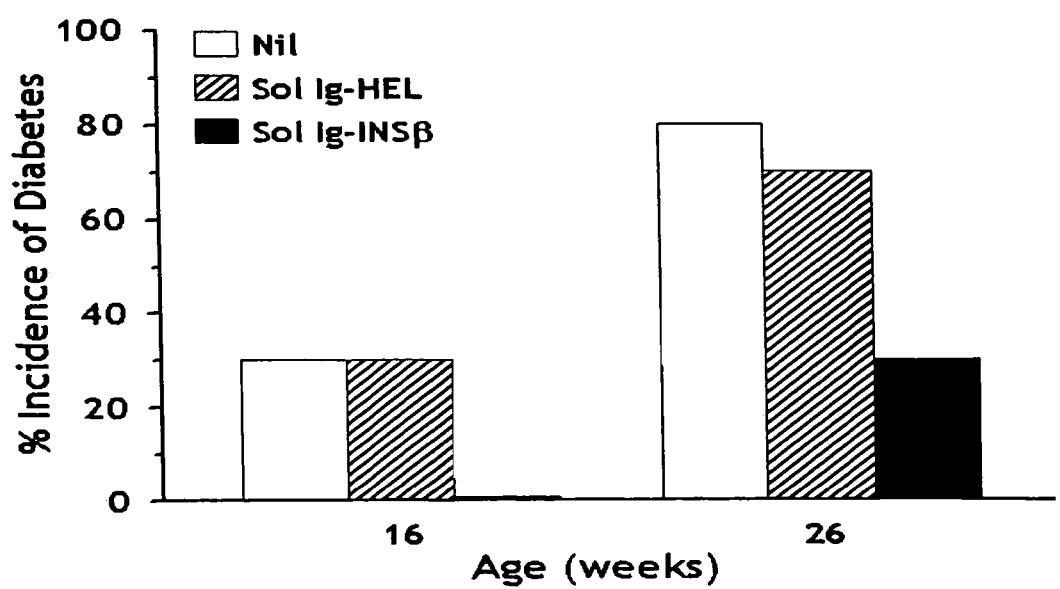
FIG. 12 shows that sustained administration of soluble Ig-INSβ to NOD mice after IAA seroconversion delays the onset of diabetes.

Results of the study, shown in FIG. 12, indicate that sustained treatment, as described above, with soluble Ig-INSβ (black bars), when administered after IAA seroconversion, significantly suppresses, delays and/or prevents the onset of diabetes by comparison with control (open bars) or Ig-HEL (hatched bars). While well over 80% of the untreated female NOD mice developed diabetes by week 26, less than 30% of mice treated repeatedly with soluble Ig-INSβ developed diabetes.

U.S. patent application Ser. No. 08/779,767, filed Jan. 7, 1997, U.S. patent application Ser. No. 10/277,264, filed Oct. 21, 2002, U.S. patent application Ser. No. 09/111,123 filed Jan. 7, 1998, U.S. patent application Ser. No. 09/623,728 filed Sep. 5, 2000, U.S. patent application Ser. No. 08/873,901 filed Jun. 4, 2001 are all hereby incorporated by reference in their entireties.

For all formulations herein, multiple doses may be proportionally compounded as is known in the art.

The invention has been described in an illustrative manner, and it is to be understood the terminology used is intended to be in the nature of description rather than of limitation. Many modifications, equivalents, and variations of the present invention are possible in light of the above teachings, therefore, it is to be understood that within the scope of the appended claims, the invention may be practiced other than as specifically described.

REFERENCES

1. Castano, L., and G. S. Eisenbarth. 1990. Type-1 diabetes: a chronic autoimmune disease of human, mouse, and rat. *Ann. Rev. Immunol.* 8:647-680.
2. Bach, J. F. 1994. Insulin-dependent diabetes mellitus as an autoimmune disease. *Endroc. Rev.* 15:516-542.
3. Tisch, R., and H. O. McDevitt. 1996. Insulin dependent diabetes mellitus. *Cell.* 85:291-297.
4. André, I., A. Gonzalez, B. Wang, J. Katz, C. Benoist, and D. Mathis. 1996. Checkpoints in the progression of autoimmune disease: lessons from diabetes models. *Proc. Natl. Acad. Sci. USA.* 93:2260-2263.
5. Delovitch, T., and B. Singh. 1997. The nonobese diabetic mouse as a model of autoimmune diabetes: immune dysregulation gets the NOD. *Immunity.* 7:727-738.
6. Makino, S., K. Kunimoto, Y. Muraoka, Y. Mizushima, K. Katagiri, and Y. Tochino. 1980. Breeding of a non-obese, diabetic strain of mice. *Jikken Dobutsu.* 29:1-13.
7. Liblau, R. S., S. M. Singer, and H. O. McDevitt. 1995. Th1 and Th2 CD4$^+$ T cells in the pathogenesis of organ-specific autoimmune diseases. *Immunol. Today.* 16:34-37.
8. Wang, B., I. André, A. Gonzalez, J. Katz, M. Aguet, C. Benoist, and D. Mathis. 1997. Interferon-γ impacts at multiple points during the progression of autoimmune diabetes. *Proc. Natl. Acad. Sci. USA.* 94:13844-13849.

9. Sarvetnick, N., J. Shizuru, D. Liggitt, L. Martin, B. McIntyre, A. Gregory, T. Parslow, and T. A. Stewart. 1990. Loss of pancreatic islet tolerance induced by β-cell expression of interferon-γ. *Nature.* 346:844-847.

10. Christen, U., T. Wolfe, U. Mohrle, A. C. Hughes, E. Rodrigo, E. A. Green, R. A. Flavell, and M. G. von Herrath. 2001. A dual role for TNF-α in type I diabetes: islet-specific expression abrogates the ongoing autoimmune process when induced late but not early during pathogenesis. *J. Immunol.* 166:7023-7032.

11. Alleva, D. G., A. Gaur, L. Jin, D. Wegmann, P. A. Gottlieb, A. Pahuja, E. B. Johnson, T. Motheral, A. Putnam, P.D. Crowe, N. Ling, S. A. Boehme, and P. J. Conlon. (2002). Immunological characterization and therapeutic activity of an altered-peptide ligand, NBI-6024, based on the immunodominant type 1 diabetes autoantigen insulin β-chain (9-23) peptide. *Diabetes.* 51: 2126-2134.

12. Quintana, F. J., A. Rotem, P. Carmi, and I. R. Cohen. 2000. Vaccination with empty plasmid DNA or CpG oligonucleotide inhibits diabetes in nonobese diabetic mince: modulation of spontaneous 60-kDa heat shock protein autoimmunity. *J. Immunol.* 16:148-155.

13. Jun, H. S., Y. H. Chung, J. Han, A. Kim, S. S. Yoo, R. S. Sherwin, and Yoon, J. W. (2002). H. S. Jun et al.: Prevention of autoimmune diabetes by GAD immunogene therapy. *Diabetologia.* 45:668-676.

14. Bot, A., D. Smith, S. Bot, A. Hughes, T. Wolfe, L. Wang, C. Woods, and M. von Herrath. 2001. Plasmid vaccination with insulin B chain prevents autoimmune diabetes in non-obese diabetic mice. *J. Immunol.* 176: 2950-2955.

15. Buschard, K., T. Bock, C. R. Pederson, S. V. Hansen, K. Aaen, M. Jorgenson, M. W. Hansen, T. W. Kjaer, I. Hageman, and K. Josefsen. 2000. Neonatal treatment with beta-cell stimulatory agents reduces the incidence of diabetes in BB rats. *Int. J. Exp. Diabetes Res.* 1:1-8.

16. Song, H. Y., M. M. Abad, C. P. Mahoney, and R. C. McEnvoy. 1999. Human insulin B chain but not A chain decreases the rate of diabetes in BB rats. *Diabetes Res. Clin. Pract.* 46:109-114.

17. Zaghouani, H., R. Steinman, R. Nonacs, H. Shah, W. Gerhard, and C. Bona. 1993. Presentation of a viral T cell epitope expressed in the CDR3 region of a self immunoglobulin molecule. *Science.* 259:224-227.

18. Legge, K. L., B. Min, N. T. Potter, and H. Zaghouani. 1997. Presentation of a T cell receptor antagonist peptide by immunoglobulins ablates activation of T cells by a synthetic peptide or proteins requiring endocytic processing. *J. Exp. Med.* 185:1043-1053.

19. Brumeanu, T.D., W. J. Swiggard, R. M. Steinman, C. A. Bona, and H. Zaghouani. 1993. Efficient loading of identical viral peptide onto class II molecules by antigenized immunoglobulin and influenza virus. *J. Exp. Med.* 178: 1795-1799.

20. Legge, K. L., J. J. Bell, L. Li, R. K. Gregg, J. C. Caprio, and H. Zaghouani. 2001. Multi-modal antigen specific therapy for autoimmunity. *Intern. Rev. Immunol.* 20:593-611.

21. Zambidis, E. T., and D. W. Scott. 1996. Epitope-specific tolerance induction with an engineered immunoglobulin. *Proc. Natl. Acad. Sci. USA.* 93:5019-5024.

22. Legge, K. L., B. Min, J. J. Bell, J. C. Caprio, L. Li, R. K. Gregg, and H. Zaghouani. 2000. Coupling of peripheral tolerance to endogenous interleukin 10 promotes effective modulation of myelin-activated T cells and ameliorates experimental allergic encephalomyelitis. *J. Exp. Med.* 191: 2039-2051.

23. Legge, K. L., R. K. Gregg, R. Maldonado-Lopez, L. Li, J. C. Caprio, M. Moser, and H. Zaghouani. 2002. On the role of dendritic cells in peripheral T cell tolerance and modulation of autoimmunity. *J. Exp. Med.* 196:217-227.

24. Balasa, B., A. La Cava, K. Van Gunst, L. Mocnik, D. Balakrishna, N. Nguen, L. Tucker, and N. Sarvetnick. 2000. A mechanism for IL-10-mediated diabetes in the nonobese diabetic (NOD) mouse: ICAM-1 deficiency blocks accelerated diabetes. *J. Immunol.* 165:7330-7337.

25. Wogensen, L., M.-S. Lee, and N. Sarvetnick. 1994. Production of interleukin 10 by islet cells accelerates immune-mediated destruction of β cells in nonobese diabetic mice. *J. Exp. Med.* 179:1379-1384.

26. Balasa, B., and N. Sarvetnick. 1996. The paradoxical effects of interleukin 10 in the immunoregulation of autoimmune diabetes. *J. Autoimmun.* 9:283-286.

27. Pennline, K. J., E. Roque-Gaffney, and M. Monahan. 1994. Recombinant human IL-10 prevents the onset of diabetes in the nonobese diabetic mouse. *Clin. Immunol. Immunopathol.* 71:169-175.

28. Phillips, J. M., N. M. Parish, M. Drage, and A. Cooke. 2001. Cutting edge: interactions through the IL-10 receptor regulate autoimmune diabetes. *J. Immunol.* 167:6087-6091.

29. Yang, Z., M. Chen, R. Wu, L. B. Fialkow, J. S. Bromber, M. McDuffie, A. Naji, and J. Nadler. 2002. Suppression of autoimmune diabetes by viral IL-10 gene transfer. *J. Immunol.* 168:6479-6485.

30. Heath, V. L., P. Hutchings, D. J. Fowell, A. Cooke, and D. Mason. 1999. Peptides derived from murine insulin are diabetogenic in both rats and mice, but the disease-inducing epitopes are different: evidence against a common environmental cross-reactivity in the pathogenicity of type 1 diabetes. *Diabetes.* 48:2157-2165.

31. Daniel, D., and D. R. Wegmann. 1996. Protection of nonobese diabetic mice from diabetes by intranasal or subcutaneous administration of insulin peptide B (9-23). *Proc. Natl. Acad. Sci. USA.* 93:956-960.

32. Serreze, D. V., H.D. Chapman, C. M. Post, E. A. Johnson, W. L. Suarez-Pinzon, and A. Rabinovitch. 2001. Th1 to Th2 cytokine shifts in nonobese diabetic mice: sometimes an outcome, rather than the cause of diabetes resistance elicited by immunostimulation. *J. Immunol.* 166:1352-1359.

33. Latek, R. R., A. Suri, S. J. Petzold, C. A. Nelson, O. Kanagawa, E. R. Unanue, and D. H. Fremont. 2000. Structural basis of peptide binding and presentation by the type 1 diabetes-associated MHC class II molecule of NOD mice. *Immunity.* 12:699-710.

34. Min, B., K. L. Legge, C. Pack, and H. Zaghouani. 1998. Neonatal exposure to a self-peptide-immunoglobulin chimera circumvents the use of adjuvant and confers resistance to autoimmune disease by a novel mechanism involving interleukin 4 lymph node deviation and interferon γ-mediated splenic anergy. *J. Exp. Med.* 188:2007-2017.

35. Romani, N., N. Bhardwaj, M. Pope, F. Koch, W. J. Swigard, U. O. Doherty, M.D. Witmer-Pack, L. Hoffman, G. Schuler, K. Inaba, and R. M. Steinman. 1996. Dendritic cells. In Weirs Handbook of Experimental Immunology. L. A. Herzenberg, D. Weir, and C. Blackwell, editors. Blackwell Science, Cambridge. 156.1-156.14.

36. Faveeuw, C., M. C. Gagnerault, and F. Lepault. 1995. Isolation of leukocytes infiltrating the islets of Langerhans of diabetes-prone mice for flow cytometric analysis. *J. Immunol. Methods.* 187:163-169.

37. Wegmann, D. R., M. Norbury-Glaser, and D. Daniel. 1994. Insulin-specific T cells are a predominant component of islet infiltrates in pre-diabetic NOD mice. *Eur. J. Immunol.* 24:1853-1857.

38. Gottlieb, P. A., and G. S. Eisenbarth. 2002. Insulin-specific tolerance in diabetes. *Clin. Immunol.* 102:2-11.

39. Yu, L., D. T. Robles, N. Abiru, P. Kaur, M. Rewers, K. Kelemen, and G. S. Eisenbarth. 2000. Early expression of antiinsulin autoantibodies of humans and the NOD mouse: evidence for early determination of subsequent diabetes. *Proc. Natl. Acad. Sci. USA.* 97:1701-1706.
40. Bonifacio, E., M. Atkinson, G. Eisenbarth, D. Serreze, T. W. Kay, E. Lee-Chan, and B. Singh. 2001. International workshop on lessons from animal models for human type 1 diabetes: identification of insulin but not glutamic acid decarboxylase or IA-2 as specific autoantigens of humoral autoimmunity in nonobese diabetic mice. *Diabetes.* 50:2451-2458.
41. Christian, C. L. 1960. Studies on aggregated gamma-globulin I & II. *J. Immunol.* 84:112-121.
42. Rosenqvist, E., T. Jossang, and J. Feder. 1987. Thermal properties of human IgG. *Mol. Immunol.* 24:495-501.
43. Groux, H., A. O'Garra, M. Bigler, M. Rouleau, J. de Vries, and M.-G. Roncarolo. 1997. Generation of a novel regulatory CD4+ T-cell population, which inhibits antigen-specific T-cell responses. *Nature.* 389:737-742.
44. Roncarolo, M. G., R. Bacchetta, C. Bordignon, S, Narula, and M. K. Levings. 2001. Type 1 T regulatory cells. *Immunol. Rev.* 182:68-79.
45. Shevach, E. M. 2000. Regulatory T cell in autoimmunity. *Ann. Rev. Immunol.* 18: 423-450
46. Asseman, C., S. Mauze, M. W. Leach, R. L. Coffman, and F. Powrie. 1999. An essential role for IL-10 in the function of regulatory T cells that inhibit intestinal inflammation. *J. Exp. Med* 190:995-1004.
47. Barrat, F. J., D. J. Cua, A. Boonstra, D. F. Richards, C. Crain, H. F. Savelkoul, R. de Waal-Malefyt, R. L. Coffman, C. M. Hawrylowicz, and A. O'Garra. 2002. In vitro generation of interleukin 10-producing regulatory CD4+ T cells is induced by immunosuppressive drugs and inhibited by T helper type 1 (Th1)- and Th2-inducing cytokines. *J. Exp. Med.* 195:603-616.
48. Zheng, X., A. Steele, W. Hancock, A. C. Stevens, P. W. Nickerson, P. Roy-Chaudhury, Y. Tian, and T. B. Strom. 1997. A noncytolytic IL-10/Fc fusion protein prevents diabetes, blocks autoimmunity, and promotes suppressor phenomena in NOD mice. *J. Immunol.* 158:4507-4513.
49. Lee, M.-S., R. Mueller, L. Wicker, L. B. Peterson, and N. Sarvetnick. 1996. IL-10 is necessary and sufficient for autoimmune diabetes in conjunction with NOD MHC homozygosity. *J. Exp. Med.* 183:2663-2668.
50. Moritani, M., K. Yoshimoto, S. Ii, M. Kondo, H. Iwahana, T. Yamaoka, T. Sano, N. Nakano, H. Kikutani, and M. Itakura. Prevention of adoptively transferred diabetes in nonobese diabetic mice with IL-10-transduced islet-specific Th1 lymphocytes. *J. Clin. Invest.* 98:1851-1859.

What is claimed is:

1. A method of preventing or delaying onset of Type 1 diabetes in a subject in need thereof, the method comprising administering to the subject a pharmaceutically acceptable composition comprising a soluble fusion protein, wherein the fusion protein comprises at least one immunoglobulin having a variable region comprising a CDR1, a CDR2, or a CDR3 region, the at least one immunoglobulin having at least one protein fragment or peptide inserted within the variable region; wherein (a) the protein fragment or peptide is GAD2 represented by SEQ. ID NO 4, (b) the subject has undergone insulin autoantibody seroconversion prior to said administering step and (c) the composition is administered to the subject in one or more dosage administrations.

2. The method of claim 1, wherein the immunoglobulin is human or humanized.

3. The method of claim 1, wherein the subject is a human subject.

4. The method of claim 1, wherein administration of the composition to the subject results in down regulation of an autoreactive T cell.

5. The method of claim 1, wherein the at least one protein fragment or peptide is inserted within a CDR region of the at least one immunoglobulin.

6. The method of claim 5, wherein administration of the composition to the subject results in substantially reduced activation of an autoreactive T cell specific for the at least one protein fragment or peptide.

7. The method of claim 1, wherein the soluble fusion protein is capable of binding to at least one Fc receptor.

8. The method of claim 7, wherein the Fc receptor is a Fcγ receptor.

9. The method of claim 7, wherein the composition is capable of being endocytosed by antigen presenting cells.

10. The method of claim 1, wherein the subject is GAD positive.

11. The method of claim 1, wherein the subject has not developed hyperglycemia at initiation of the administering step.

12. The method of claim 1, wherein the subject expresses a Type 1 diabetes predisposition marker at initiation of the administering step.

13. The method of claim 1, wherein upon administration of the composition to the subject, the subject undergoes a dose dependent suspension, prevention, or delay in onset of Type 1 diabetes.

14. The method of claim 1, wherein administration of a first dosage of the composition occurs before the subject has developed type-1 diabetes.

15. The method of claim 2 wherein the immunoglobulin is selected from the group consisting of IgG1, IgG2, IgG2a, IgG2b, IgG3, IgG4, IgGA, IgA1, IgA2, IgGE, IgD, IgE, or IgM.

16. The method of claim 5 wherein the at least one protein fragment or peptide is inserted within the CDR3 region of the immunoglobulin.

17. The method of claim 16 wherein the at least one protein fragment or peptide is inserted within the CDR3 region of the immunoglobulin in place of a D segment.

18. The method of claim 1 wherein the at least one protein fragment or peptide consists of amino acid residues 524-543 of GAD65.

19. The method of claim 1 wherein the at least one protein fragment or peptide consists of amino acid residues 206-220 of GAD65.

20. The method of claim 1 wherein the subject is a human.

21. The method of claim 1 wherein the pharmaceutical composition further comprises at least one pharmaceutically acceptable carrier.

22. The method of claim 21 wherein the composition comprises an aqueous solution or suspension.

23. The method of claim 22 where the administering step is accomplished by injection or infusion.

* * * * *

```
                         SEQUENCE LISTING

<160> NUMBER OF SEQ ID NOS: 12

<210> SEQ ID NO 1
<211> LENGTH: 15
<212> TYPE: PRT
<213> ORGANISM: Artificial Sequence
<220> FEATURE:
<223> OTHER INFORMATION: Amino acid residues 9-23 of insulin beta chain

<400> SEQUENCE: 1

Ser His Leu Val Glu Ala Leu Tyr Leu Val Cys Gly Glu Arg Gly
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Amino acid residues 11-25 of Hen Egg Lysosyme

<400> SEQUENCE: 2

Ala Met Lys Arg His Gly Leu Asp Asn Tyr Arg Gly Tyr Ser Leu
1               5                   10                  15

<210> SEQ ID NO 3
<211> LENGTH: 20
<212> TYPE: PRT
<213> ORGANISM: Artificial Sequence
<220> FEATURE:
<223> OTHER INFORMATION: Amino acid residues 524-543 of GAD 65

<400> SEQUENCE: 3

Ser Arg Leu Ser Lys Val Ala Pro Val Ile Lys Ala Arg Met Met Glu
1               5                   10                  15

Tyr Gly Thr Thr
            20
```

```
<210> SEQ ID NO 4
<211> LENGTH: 15
<212> TYPE: PRT
<213> ORGANISM: Artificial Sequence
<220> FEATURE:
<223> OTHER INFORMATION: Amino acid residues 206-220 of GAD 65

<400> SEQUENCE: 4

Thr Tyr Glu Ile Ala Pro Val Phe Val Leu Leu Glu Tyr Val Thr
1               5                   10                  15

<210> SEQ ID NO 5
<211> LENGTH: 14
<212> TYPE: PRT
<213> ORGANISM: Artificial Sequence
<220> FEATURE:
<223> OTHER INFORMATION: Flanking region within heavy chain CDR3 of
      91A3 Ig

<400> SEQUENCE: 5

Tyr Phe Cys Ala Arg Ser Tyr Tyr Ser Gly Asp Met Tyr Cys
1               5                   10

<210> SEQ ID NO 6
<211> LENGTH: 4
<212> TYPE: PRT
<213> ORGANISM: Artificial Sequence
<220> FEATURE:
<223> OTHER INFORMATION: Flanking region within heavy chain CDR3 of
      91A3 Ig

<400> SEQUENCE: 6

Phe Asp Tyr Trp
1

<210> SEQ ID NO 7
<211> LENGTH: 42
<212> TYPE: DNA
<213> ORGANISM: Artificial Sequence
<220> FEATURE:
<223> OTHER INFORMATION: Flanking region within heavy chain CDR3 of
      91A3 Ig

<400> SEQUENCE: 7
tatttctgtg caagatcgta ttactctggt gatatgtact gc                          42

<210> SEQ ID NO 8
<211> LENGTH: 12
<212> TYPE: DNA
<213> ORGANISM: Artificial Sequence
<220> FEATURE:
<223> OTHER INFORMATION: Flanking region within heavy chain CDR3 of
      91A3 Ig

<400> SEQUENCE: 8
tttgactact gg                                                           12

<210> SEQ ID NO 9
<211> LENGTH: 14
<212> TYPE: PRT
<213> ORGANISM: Artificial Sequence
<220> FEATURE:
<223> OTHER INFORMATION: 91A3H-Insulin beta insert
<220> FEATURE:
<221> NAME/KEY: misc_feature
<222> LOCATION: (7)..(7)
<223> OTHER INFORMATION: Xaa can be any naturally occurring amino acid
```

```
<400> SEQUENCE: 9

His Leu Val Glu Ala Leu Xaa Leu Val Cys Gly Glu Arg Gly
1               5                   10

<210> SEQ ID NO 10
<211> LENGTH: 45
<212> TYPE: DNA
<213> ORGANISM: Artificial Sequence
<220> FEATURE:
<223> OTHER INFORMATION: Insulin beta insert sequence
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (22)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t

<400> SEQUENCE: 10
agccncctag tgnagncgcn tnnnctngtt tgcggtgaaa gaggt              45

<210> SEQ ID NO 11
<211> LENGTH: 15
<212> TYPE: PRT
<213> ORGANISM: Artificial Sequence
<220> FEATURE:
<223> OTHER INFORMATION: 91A3H-HEL insert

<400> SEQUENCE: 11

Ala Met Lys Arg His Gly Leu Asp Asn Tyr Arg Gly Tyr Ser Leu
1               5                   10                  15

<210> SEQ ID NO 12
<211> LENGTH: 45
<212> TYPE: DNA
<213> ORGANISM: Artificial Sequence
<220> FEATURE:
<223> OTHER INFORMATION: 91A3H-HEL insert
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
```

```
<220> FEATURE:
<221> NAME/KEY: misc_feature
<222> LOCATION: (27)..(27)
<223> OTHER INFORMATION: n is a, c, g, or t

<400> SEQUENCE: 12
gcaatgangc gccacnggan agnnaantat cggggatata gcctc                    45
```